(12) United States Patent
Bisgaier et al.

(10) Patent No.: US 7,435,717 B2
(45) Date of Patent: Oct. 14, 2008

(54) PHARMACEUTICAL FORMULATIONS, METHODS, AND DOSING REGIMENS FOR THE TREATMENT AND PREVENTION OF ACUTE CORONARY SYNDROMES

(75) Inventors: Charles L. Bisgaier, Ann Arbor, MI (US); Narendra D. Lalwani, South Lyon, MI (US); Wendi V. Rodrigueza, Roslindale, MA (US); Daniel Hartman, Brighton, MI (US); Jan Johansson, Milpitas, CA (US)

(73) Assignee: Pfizer Inc., New York, NY (US)

( * ) Notice: Subject to any disclaimer, the term of this patent is extended or adjusted under 35 U.S.C. 154(b) by 163 days.

(21) Appl. No.: 10/967,061

(22) Filed: Oct. 15, 2004

(65) Prior Publication Data
US 2005/0142180 A1 Jun. 30, 2005

Related U.S. Application Data

(60) Provisional application No. 60/571,129, filed on May 14, 2004, provisional application No. 60/517,016, filed on Nov. 3, 2003, provisional application No. 60/513,116, filed on Oct. 20, 2003.

(51) Int. Cl.
*A61K 38/00* (2006.01)
(52) U.S. Cl. ........................................................ 514/2
(58) Field of Classification Search ........................ None
See application file for complete search history.

(56) References Cited

U.S. PATENT DOCUMENTS

| | | | |
|---|---|---|---|
| 5,876,968 A | 2/1999 | Sirtori et al. | |
| 6,617,134 B1 | 9/2003 | Sirtori et al. | |
| 2003/0109442 A1 | 6/2003 | Bisgaier et al. | |

OTHER PUBLICATIONS

Cole et al., Method-dependent changes in "HDL-cholesterol" with recombinant apolipoprotein A-l(Milano) infusion in healthy volunteers, Clin Chem. 2002, vol. 48. No. 4, pp. 680-681.*
Rioufol, G., et al, "Multiple Atherosclerotic Plaque Rupture in Acute Coronary Syndrome; A Three-Vessel Intravascular Ultrasound Study", Circulation, 2002; 106; pp. 804-808.
Timmis, Adam, "Plaque Stabilisation in Acute Coronary Syndromes: Clinical Considerations", Heart; 2003; 89; pp. 1268-1272.
Franceschini, G., et al, "A-l Milano Apoprotein; Decreased High Density Lipoprotein Cholesterol Levels With Significant Lipoprotein Modifications and Without Clinical Atherosclerosis in an Italian Family", J. Clin. Invest., 1980; 66; pp. 892-900.
Weisgraber, K., et al, "Apolipoprotein A-l Milano—Detection of Normal A-l in Affected Subjects and Evidence for a Cysteine for Arginine Substitution in the Variant A-l*", The Journal of Biological Chemistry, 1983; 258; 4; pp. 2508-2513.
Franceschini, G., et al, "Apolipoprotein A-l Milano; Correlation between High Density Lipoprotein Subclass Distribution and Triglyceridemia", Arteriosclerosis; 1987; 7; pp. 426-435.
Ameli, S., et al, "Recombinant Apolipoprotein A-l Milano Reduces Intimal Thickening After Balloon Injury in Hypercholesterolemic Rabbits", Circualtion, 1994; 90; pp. 1935-1941.
Shah, P., et al, "Effects of Recombinant Apolipoprotein A-l Milano on Aortic Atherosclerosis in Apolipoprotein E-Deficient Mice", Circulation, 1998; 97; pp. 780-785.
Shah, P., et al, "High-Dose Recombinant Apolipoprotein A-l Milano Mobilizes Tissue Cholesterol and Rapidly Reduces Plaque Lipid and Macrophage Content in Apolipoprotein E-Deficient Mice—Potential Implications for Acute Plaque Stabilization", Circulation, 2001; 103; pp. 3047-3050.
Li, D., et al, "Inhibition of Arterial Thrombus Formation by ApoAl Milano", Arterloscler Thromb Vasc Biol., 1999; 19; pp. 378-383.
Newton, R., et al, "HDL therapy for the acute treatment of atherosclerosis", Atherosclerosis Supplements, 2002; 3; pp. 31-38.
Chiesa, G., et al, "Recombinant Apolipoprotein A-l Milano Infusion Into Rabbit Carotid Artery Rapidly Removes Lipid From Fatty Streaks", Circ Res., 2002; 90; pp. 974-980.
Soma, M., et al, "Recombinant Apolipoprotein A-l Milano Dimer Inhibits Carotid Intimal Thickening Induced by Perivascular Manipulation in Rabbits", Cir. Res., 76, 1995; pp. 405-411.
Qiao, J., et al., Pathology of Atheromatous Lesions in Inbred and Genetically Engineered Mice, *Arteriosclerosis and Thrombosis*, vol. 14(9):1480-1497, 1994.
Warnick, G., et al., Evolution of Methods for Measurement of HDL-cholesterol: From Ultracentrifugation to Homogeneous Assays, *Clinical Chemistry*, vol. 47(9): 1579-1596, 2001.
Sviridov, et al., Journal of Lipid Research, vol. 43, pp. 1283-1292 (2002).

* cited by examiner

*Primary Examiner*—Robert B. Mondesi
(74) *Attorney, Agent, or Firm*—Gregg C. Benson; Nicholas I. Slepchuk, Jr.

(57) ABSTRACT

The invention provides methods and formulations for treating and preventing acute coronary syndromes. The methods of the instant invention provide safe and effective doses of an Apolipoprotein A-I Milano:phospholipid complex to reduce and stabilize atherosclerotic plaque. Pharmaceutical formulations of the Apo A-I Milano:phospholipid complexes are also provided.

55 Claims, 19 Drawing Sheets

Figure 1:
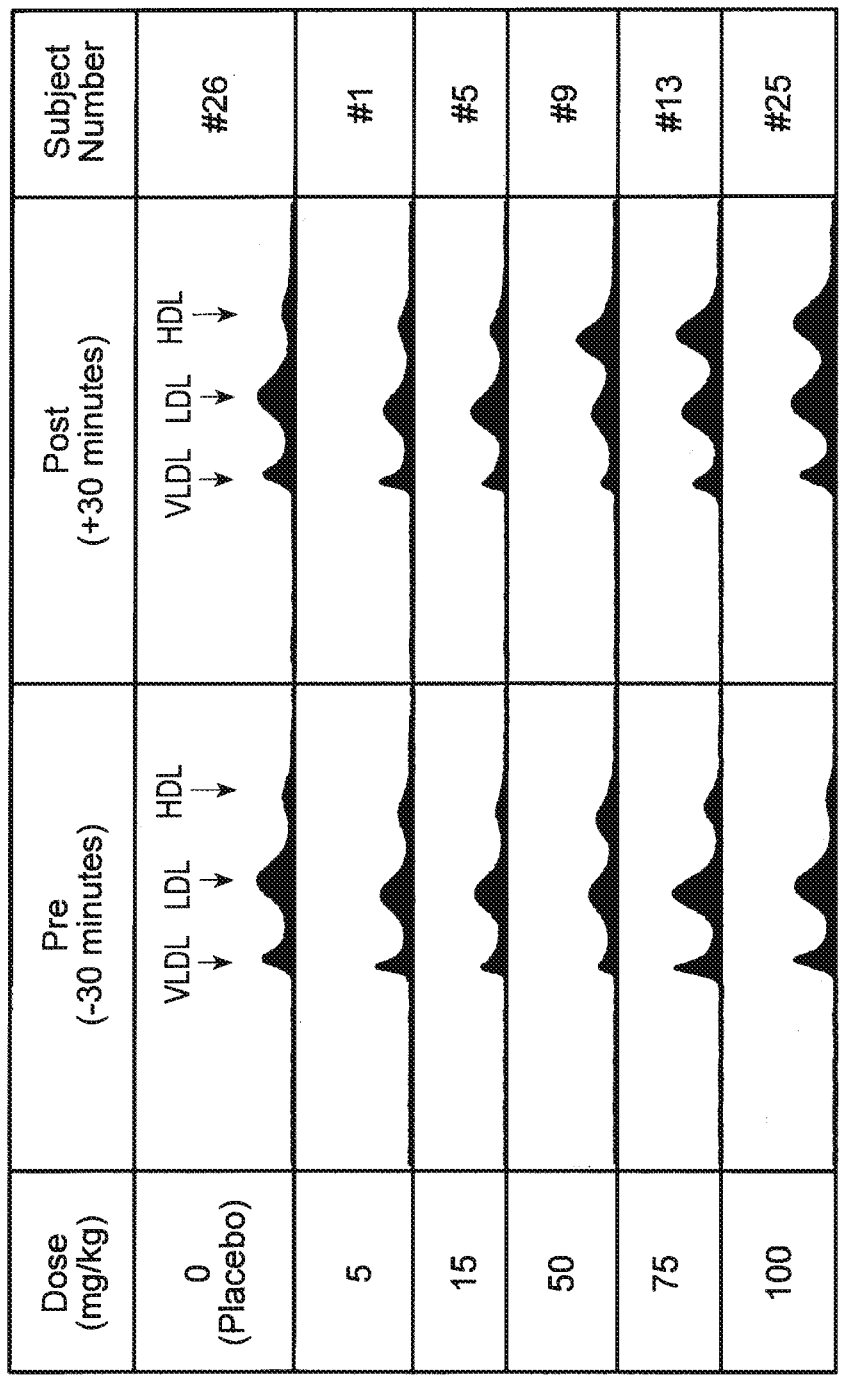

FIG. 3A  FIG. 3B
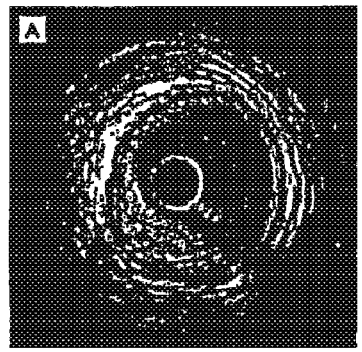 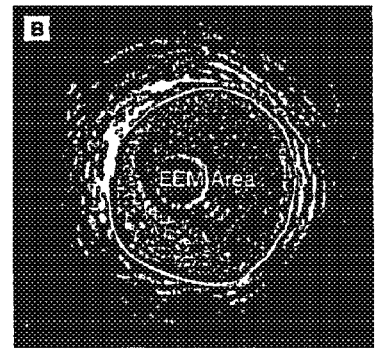
FIG. 3C  FIG. 3D
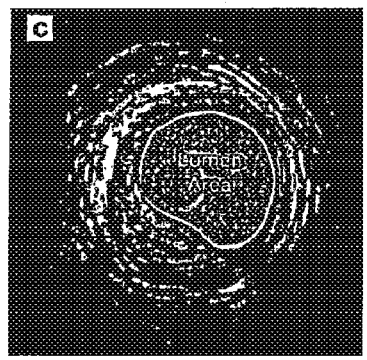 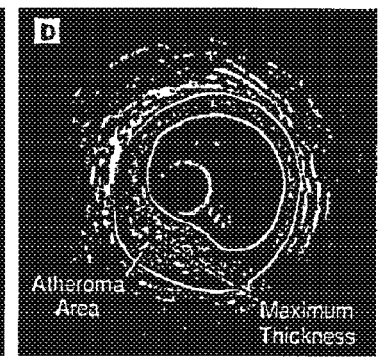
FIG. 4A  FIG. 4B
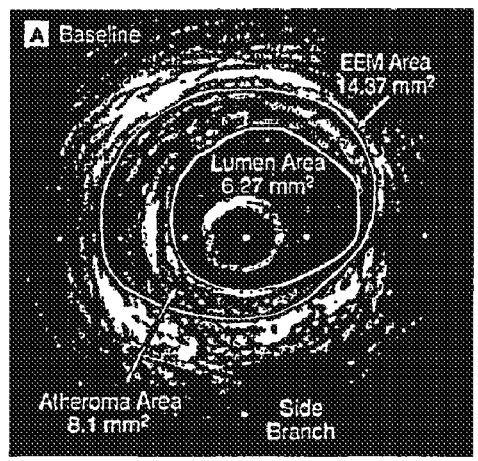 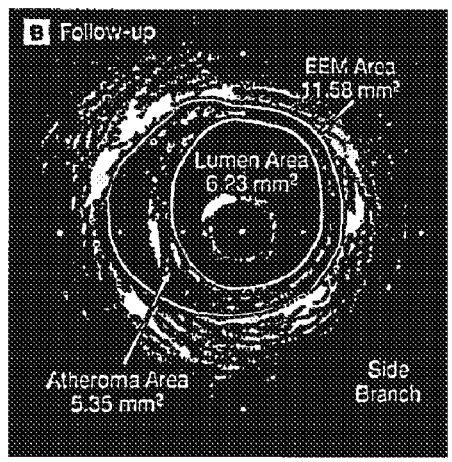

FIG. 12
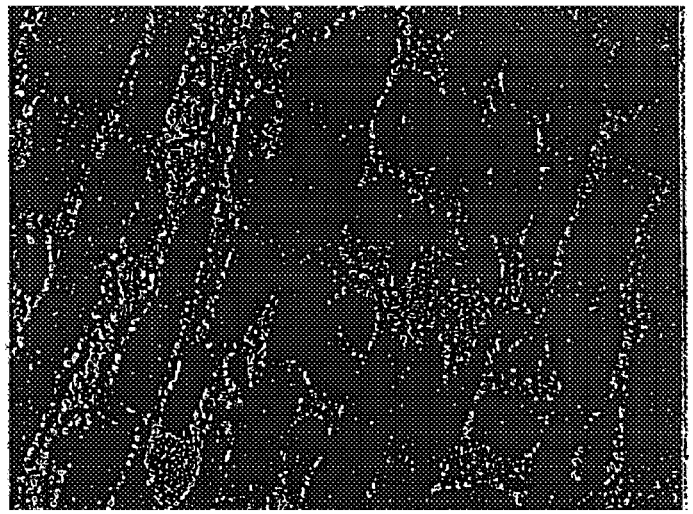
VEHICLE
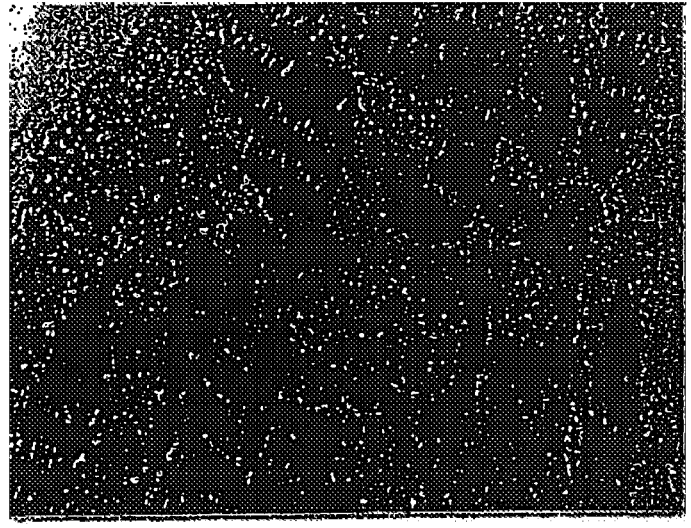
ETC-216

FIG. 13
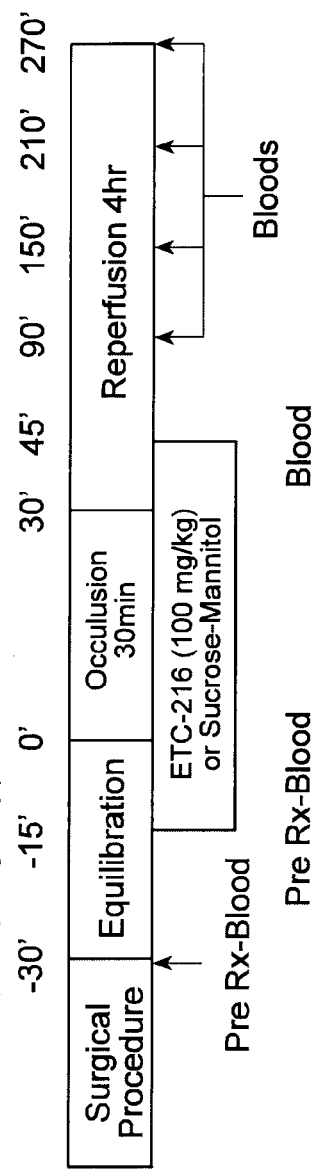
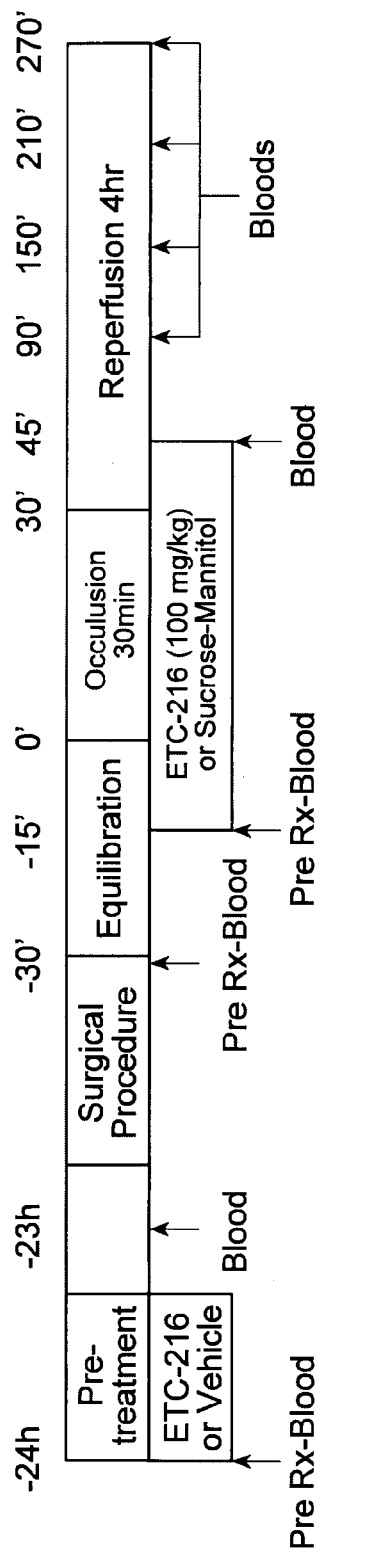

PHARMACEUTICAL FORMULATIONS, METHODS, AND DOSING REGIMENS FOR THE TREATMENT AND PREVENTION OF ACUTE CORONARY SYNDROMES

This application is related to U.S. Provisional Application Ser. Nos. 60/513,116 (filed Oct. 20, 2003), 60/517,016 (filed Nov. 3, 2003) and 60/571,129 (filed May 14, 2004), each of which is incorporated herein by reference in its entirety.

1. TECHNICAL FIELD

The invention provides novel formulations and methods to treat or prevent acute coronary syndromes. In a preferred embodiment, the formulations are single unit dosages that have a specified pH, osmolality and purity. In a preferred method, the formulation is administered weekly, monthly or yearly in a dose range of about 1 mg/kg to about 100 mg/kg per administration. Additionally, doses and dosing regimens are disclosed as well as specific diseases for which the doses or dosing regimens are intended to be used. The formulations and methods employ an Apolipoprotein A-I Milano:phospholipid complex.

2. BACKGROUND OF THE INVENTION

The management and treatment of myocardial infarction has changed dramatically since the first half of the 20$^{th}$ century, progressing from an era of bed rest and observation, to an emphasis on technology, including hemodynamic monitoring and balloon catheters, to an increased focus on thrombolytic therapy. (Antman and Braunwald, "Acute Myocardial Infarction" in Heart Disease, A Textbook of Cardiovascular Medicine, 6$^{th}$ edition, vol. 2, Braunwald et al., eds, 2001, W. B. Saunders Company, Philadelphia). Therapeutic approaches to treating cardiovascular diseases have evolved tremendously in the last 100 years accompanied by greater understanding of the underlying pathology.

Almost all myocardial infarctions result from coronary atherosclerosis, generally with superimposed coronary thrombosis. Slowly accumulating plaques can be asymptomatic due to the development of collateral vessels. However, atherosclerotic plaques, especially those rich in lipids, are prone to abrupt plaque rupture. Plaque rupture and associated endothelial injury cause the release of mediators such as thromboxane $A_2$, serotonin, adenosine diphosphate, thrombin, platelet activating factor, tissue factor and oxygen-derived free radicals. These mediators promote platelet aggregation and mechanical obstruction often leading to thrombus formation which interferes with blood flow and oxygen supply. Persistent and severe interferences with myocardial oxygen supply can lead to acute myocardial infarction. (See, Rioufol et al., 2002, *Circulation* 106: 804, Timmis, 2003, *Heart* 89:1268-72).

The mainstay of atherosclerotic pharmacotherapy has been chronic therapy to prevent or slow the development of atherosclerotic plaques primarily by focusing on lowering LDL or "bad cholesterol" as a therapeutic endpoint. Statin therapy, for example, has greatly contributed to improved cardiovascular health; however, adverse effects such as rhabdomyolysis, remain an impediment. Furthermore, statins do little in an acute situation, for example, to reduce vulnerable, unstable atherosclerotic plaque during an ischemic episode. Acute treatment has largely relied on thrombolytics (such as tPA) and surgical intervention such as percutaneous transluminal coronary angioplasty (PTCA) and coronary artery bypass graft (CABG). While thrombolytics provide relief by decreasing or eliminating an occluding thrombus, they do not alter the underlying pathology. Interventions such as PTCA carry their own risks and are often unsuitable for patients in acute conditions. Hence current pharmacologic therapies do little to help patients once unstable plaque presents as a risk. (See, Newton and Krause 2002, *Atherosclerosis* S3:31-38).

HDL therapy is emerging as a new treatment paradigm for dyslipidemia and atherosclerosis. Id. Apolipoprotein A-I Milano (Apo A-I Milano) has been of interest due to the paradoxical finding that carriers of the variant form of this apolipoprotein have low HDL ("good cholesterol") levels and decreased risk of cardiovascular disease. (See, Franceschini et al., 1980, *J. Clin. Invest.* 66:892-900, Weisgraber et al., 1983, *J. Biol. Chem.* 258: 2508-2513, Franceschini et al., 1985, *Atherosclerosis* 58: 159-174, Franceschini et al., 1987, *Arteriosclerosis* 7:426-435). Apo A-I Milano homodimers were found to reduce intimal thickening in cholesterol fed rabbits (Ameli et al., 1994, *Circulation*, 90: 1935-41 and Soma et al., 1995, *Cir. Res.* 76:405-11). In ApoE deficient mice, atherosclerotic lesions were reduced by both multiple low dose and single high dose Apo A-I Milano:lipid complexes (Shah et al., 1998, *Circulation* 97: 780-85 and Shah et al., 2001, *Circulation* 103:3047-50). Plaque regression in rabbits was also demonstrated with single local infusions of Apo A-I Milano:phospholipid complexes in doses of 500 mg and 1000 mg of protein per rabbit. (Chiesa et al., 2002, *Cir. Res.* 90:974-80). The lesions induced in the rabbit model are largely comprised of macrophages and not representative of the more complex lesions in humans. Therefore, it is uncertain if analogous treatments would be effective for the complicated plaques found in human atherosclerosis. (Li et al., 1999, *Arterioscler Thromb Vasc Biol* 19:378-383 and Shah et al., 2001, *Circulation* 103:3047-50).

Yet despite the improved understanding of the pathophysiology of myocardial infarction and developments in HDL therapy, safe and effective doses, dosing regimens and pharmaceutical formulations for the prophylactic and therapeutic use of Apo A-I Milano or Apo A-I Milano:lipid complexes in humans are still desired.

3. SUMMARY OF THE INVENTION

The invention provides methods and pharmaceutical formulations for the treatment and prevention of cardiovascular disease or related disorders including atherosclerosis, acute coronary syndromes, ischemia, ischemic reperfusion injury, angina and myocardial infarction and the reduction or stabilization of atherosclerotic plaque, the reduction of plaque in occluded vessels and promotion of cholesterol efflux. The invention thus encompasses doses and dosing regimens for the use of Apo A-I Milano:phospholipid complex and pharmaceutical formulations of Apo A-I Milano:phospholipid complex to treat or prevent cardiovascular disease or related disorders including atherosclerosis, acute coronary syndromes, ischemic reperfusion injury, angina and myocardial infarction, and the reduction or stabilization of atherosclerotic plaque, the reduction of plaque in occluded vessels and promotion of cholesterol efflux. The method and formulations described herein cause rapid reduction or stabilization of unstable atherosclerotic plaques which, if left untreated or treated by conventional methods, can rupture and lead to ischemic events including acute coronary syndromes.

Applicants have determined that an exogenously produced HDL mimetic, such as Apo A-I Milano, preferably as an Apo A-I Milano:phospholipid complex, offers a unique approach for the treatment and prevention of cardiovascular disease or related disorders; such disorders include but are not limited to atherosclerosis, acute coronary syndromes, ischemia, ischemic reperfusion injury, angina and myocardial infarction, or the reduction or stabilization of atherosclerotic plaque in narrowed or occluded vessels. The methods including the doses and dosing regimens and pharmaceutical formulations of the invention provide safe, effective and non-surgical treatment which rapidly promotes cholesterol efflux and mobilization from atherosclerotic plaques. The promotion of rapid cholesterol efflux reduces atheroma volume in one or more affected vessels. Reduced atheromas (the mass of plaque of degenerated thickened arterial intima occurring in atherosclerotic vessels) allow greater blood flow and reduces the risk of ischemia, including unstable angina, myocardial infarctions and acute coronary syndromes.

Prior to this invention which provides pharmaceutical formulations of Apo A-I M and specific doses for the treatment and prevention of cardiovascular disease, including acute coronary syndromes, atherosclerosis, angina, myocardial infarction, and ischemic reperfusion injury, conventional atherosclerotic therapy focused on lowering LDL or "bad cholesterol" as a therapeutic endpoint. These conventional LDL therapies, for example, treatment with statins, can require months of treatment before LDL serum levels are decreased in a subject. In acute or emerging cardiovascular disorders, conventional therapy has largely relied on surgical intervention such as percutaneous transluminal coronary angioplasty (PTCA) and coronary artery bypass graft (CABG). However, surgical intervention is often contraindicated in some patients in an emergent situation, particularly patients in poor overall health. Moreover, these conventional methods do not provide a non-surgical, pharmacologic treatment effective in an acute situation. Furthermore, conventional therapies focused on treating the symptoms of cardiovascular disease and acute coronary syndromes especially in the circulatory system. Conventional therapies as described above and in more detail below, have focused on reducing LDL cholesterol, reducing blood clot formation and lowering blood pressure which do not treat or prevent the underlying cause of cardiovascular disease and acute coronary syndromes, the stabilization, reduction and modification of the plaque within the vessel wall.

The pharmaceutical formulations and methods, including the doses and dosing schedules provided herein are safe, effective and act rapidly to reduce or stabilize atherosclerotic plaque. The doses described herein are rapid acting, providing reduction of atherosclerotic plaque in as little as a few weeks by promoting cholesterol mobilization. In certain embodiments, the doses described herein can be used to treat a subject suffering from acute coronary syndromes or disorders associated with ischemia or vessel occlusion. In certain embodiments, the doses described herein can be used to prevent disease progression once atherosclerotic plaques present a risk to the subject. The disease progression prevented can be further occlusion of a vessel or to prevent the rupture of an unstable atherosclerotic plaque which can lead to ischemic conditions including acute coronary syndromes and ischemic reperfusion injury.

The methods and pharmaceutical formulations provided herein are so effective that a single dose of 45 mg/kg can stimulate cholesterol mobilization from an atherosclerotic plaque. In certain embodiments, a single high dose, for example about 45 mg/kg, of the Apo A-I Milano:phospholipid complex or pharmaceutical formulation thereof, can be administered to a subject. In certain embodiments, one or more high doses of the Apo A-I Milano:phospholipid complex or pharmaceutical formulation thereof, can be administered to a subject followed by one or more of the same dose (45 mg/kg) or lower doses, for example, about 1 mg/kg, about 3 mg/kg, about 5 mg/kg, about 10 mg/kg or about 15 mg/kg. For example, a subject may be administered two doses of 45 mg/kg and then additional doses of 10 mg/kg. Additionally, the oppose regimen of low dose followed by high dose may be used. Of course, for acute disease condition the higher doses are preferably used first. In certain embodiments, the subject can be treated once weekly for several weeks with the Apo A-I Milano:phospholipid complex or pharmaceutical formulation thereof and then treated on an intermittent bases, for example, twice yearly, yearly or every two years, as needed to maintain patent and non-occluded vessels, and to reduce the risk of plaque rupture and adverse vascular events.

In certain embodiments, the methods for the treatment or prevention of acute coronary syndromes comprise administering Apo A-I Milano:phospholipid complexes or pharmaceutical formulations thereof about every day, about every other day, about every 3 days, about every 4 days, about every 5 days, about every 6 days, about every 7 days, about every 8 to 10 days or about every 11 to 14 days to a subject in need thereof. In a preferred embodiment, the Apo A-I Milano:phospholipid complexes or pharmaceutical formulations thereof can be administered about every 7 days. In certain embodiments, administration of the Apo A-I Milano:phospholipid complexes or pharmaceutical formulations thereof can be a one time administration. In certain embodiments, administration can continue for about 1 week, about 2 weeks, about 3 weeks, about 4 weeks, about 5 weeks, about 6 weeks, about 7-12 weeks, about 13-24 weeks or about 25-52 weeks. In certain preferred embodiments, administration of the Apo A-I Milano:phospholipid complexes or pharmaceutical formulations thereof is about every 7 days for about 5 weeks. In certain embodiments, administration can be intermittent after, for example, about 5 weeks. For example, a subject can be treated once a week for about 5 weeks and then treated about 3 to about 4 times over the following year. In certain embodiments, the pharmaceutical formulations described herein can be administered to the subject intermittently to maintain the patency of a vessel. For example, a dose of about 15 mg/kg can be administered to the pharmaceutical formulation administration about every 10 days for about 7 weeks and then treated, for example, about 26 weeks later or about 52 weeks later. Other embodiments, including dosing schedules and use of the methods in combination with conventional drug therapy and surgical interventions are described hereinbelow.

The invention provides pharmaceutical formulations for administration of Apolipoprotein A-I Milano (Apo A-I Milano) for the treatment or prevention of acute coronary syndromes and ischemic reperfusion in jury. In a preferred embodiment the Apo A-I Milano is complexed with a lipid for the methods described herein. For example, the lipid can be a phospholipid, preferably 1-palmitoyl-2-oleoyl-sn-glycero-3-phosphocholine (also termed, 1-palmitoyl-2-oleoyl-phosphatidylcholine or POPC). In a most preferred embodiment, the Apo A-I Milano:POPC complex can be a pharmaceutical formulation. In another preferred embodiment, the Apo A-I Milano:phospholipid complex or a pharmaceutical formulation thereof can be administered in a dose of about 1 mg of protein/kg to about 100 mg of protein/kg to a subject in need thereof.

In certain embodiments, the methods can comprise administering doses of the Apo A-I Milano:phospholipid complexes or injectable or liquid pharmaceutical formulations thereof for the treatment of acute coronary syndromes. In a preferred embodiment, the ApoAI M:phospholipid complexes or pharmaceutical formulations thereof can be administered in a dose of about 1 mg (protein)/kg to about 100 mg (protein)/kg to a subject in need thereof. In certain embodiments, the method can comprise treatment or prevention of acute coronary syndromes by the administration of Apo A-I Milano:phospholipid complexes or pharmaceutical formulations thereof as an intravenous infusion. In certain embodiments, the methods can comprise administration as a intravenous push infusion. By intravenous push infusion, it is meant that the Apo A-I Milano:phospholipid or pharmaceutical formulations thereof are administered intravenously over a short time period such as up to 5 minutes, for example, 2-5 minutes. In certain embodiments, administration of the Apo A-I Milano:phospholipid complexes or pharmaceutical formulations thereof can comprise a continuous intravenous infusion. By continuous intravenous infusion it is meant that Apo A-I Milano:phospholipid complexes or pharmaceutical formulations thereof are administered continuously over a period of time longer than 2-5 minutes, for example, about 30 minutes to about 3 hours. Continuous intravenous infusions can be administered with the aid of an infusion pump or device. In certain embodiments, administration of the Apo A-I Milano: phospholipid or pharmaceutical formulations thereof can be a combination of continuous intravenous infusions and intravenous push infusions ("bolus doses") of the Apo A-I Milano: phospholipid complexes or pharmaceutical formulations thereof. The bolus doses can be administered before, after or during the continuous infusion. In certain embodiments the administration of the Apo A-I Milano or lipid complexes or pharmaceutical formulations thereof can be in combination with other drugs that treat or prevent cardiovascular disease, concomitant or comorbid diseases or provide symptomatic relief. The administration of other drugs can be concurrent or sequential.

The methods provide for intravenous infusion of the pharmaceutical formulations described herein. Any suitable vessel can be used for infusion, including peripheral vessels such as the vessels in the antecubital fossa of the arm or a central line into the chest. In preferred embodiments, the pharmaceutical formulation is infused into the cephalic or median cubital vessel at the antecubital fossa in the arm of a subject.

In certain embodiments, the methods can comprise administration of a pharmaceutical formulation of the Apo A-I Milano:phospholipid complex at high or low doses or a combination thereof. As described hereinbelow, a high dose of the pharmaceutical formulation over a short dosing interval can safely and effectively reduce atheroma volume in subjects with partially or fully occluded vessels. In certain embodiments, the pharmaceutical formulation can be administered before, during or after a surgical intervention such as PTCA to unblock an occluded vessel. In certain embodiments, one or more intermittent doses can be administered to the subject to maintain the patency of a previously occluded vessel ("maintenance dose").

This invention provides a novel approach to the treatment or prevention of ischemic reperfusion injury, that is, the use of the pharmaceutical formulations or doses of Apo A-I Milano complex described herein for the treatment of ischemic reperfusion. Doses useful for this treatment include doses up to 100 mg/kg of the Apo A-I Milano:phospholipid complex administered to a subject in need thereof. In certain embodiments, the methods can comprise administration of a pharmaceutical composition of the Apo A-I Milano: phospholipid complex at a dose of about 1 mg/kg to about 100 mg/kg of a subject's body weight. In particular embodiments, the methods can comprise administration of a pharmaceutical composition of the Apo A-I Milano:phospholipid complex at a dose of about 10 mg/kg to about 50 mg/kg. In a preferred embodiment, the methods can comprise administration of a pharmaceutical composition of the Apo A-I Milano:phospholipid complex at a specific dose of about 15 mg/kg. In another preferred embodiment, the methods can comprise administration of a pharmaceutical composition of the Apo A-I Milano:phospholipid complex at a specific dose of about 45 mg/kg. The invention also preferably includes the use of 15 mg/kg alone or in combination with the 45 mg/kg dose. Similarly, the 45 mg/kg dose can be used alone or in combination with the 15 mg/k-g dose for the treatment or prevention of ischemic reperfusion injury.

The pharmaceutical formulation provided herein comprises an Apo A-I Milano:phospholipid complex of suitable pH, osmolality, tonicity, purity and sterility to allow safe administration to a subject. The pharmaceutical formulations can be formulated for a single, one-time use or can be formulated to contain antimicrobial excipients, as described below, rendering the pharmaceutical formulations suitable for multiple doses. In certain embodiments, the pharmaceutical formulation can be in sterile pre-filled syringes or sterile pre-filled bags which can be frozen or refrigerated. In preferred embodiments, the Apo A-I Milano:lipid complex is an Apo A-I Milano:phospholipid complex. In more preferred embodiments, the Apo A-I Milano:phospholipid complex is Apo A-I Milano:POPC.

In certain embodiments, the pharmaceutical formulation can be in unit dose or unit-of-use packages. As is known to those of skill in the art, a unit dose package provides delivery of a single dose of a drug to a subject. The methods of the invention provide for a unit dose package of a pharmaceutical formulation comprising, for example, 1050 mg of Apo A-I Milano protein per package. For example, the 1050 mg of Apo A-I Milano protein, is an amount that administers 15 mg/kg of Apo A-I Milano to a 70 kg subject. The unit can be, for example, a sterile single use vial, a sterile pre-filled syringe, sterile pre-filled bags (i.e. piggybacks) and the like.

In certain embodiments, the pharmaceutical formulation can be a unit-of-use package. As is known to those of skill in the art, a unit-of-use package is a convenient, prescription size, patient ready unit labeled for direct distribution by health care providers. A unit-of-use package contains a pharmaceutical formulation in an amount necessary for a typical treatment interval and duration for a given indication. The methods of the invention provide for a unit-of-use package of a pharmaceutical formulation comprising, for example, Apo A-I Milano:phospholipid complex in an amount sufficient to treat an average sized adult male or female with 15 mg/kg of Apo A-I Milano protein intravenously once weekly for 5 weeks. Thus a unit of use package as described above would have five doses of Apo A-I Milano:phospholipid complex (available in a vial or pre-filled syringes). In one embodiment, the unit-of-use package can comprise a pharmaceutical formulation comprising the Apo A-I Milano:phospholipid complex in an amount sufficient to treat an average sized adult male or female with a dose of 15 mg/kg or 45 mg/kg once weekly for 6 weeks. It will be apparent to those of skill in the art that the doses described herein are based on the subject's body weight.

The pharmaceutical formulations can be labeled and have accompanying labeling to identify the formulation contained therein and other information useful to health care providers and subjects in the treatment of acute coronary syndromes, including, but not limited to, instructions for use, dose, dosing interval, duration, indication, contraindications, warnings, precautions, handling and storage instructions and the like.

4. BRIEF DESCRIPTION OF THE FIGURES

Figure 2A:
Figure 2D:
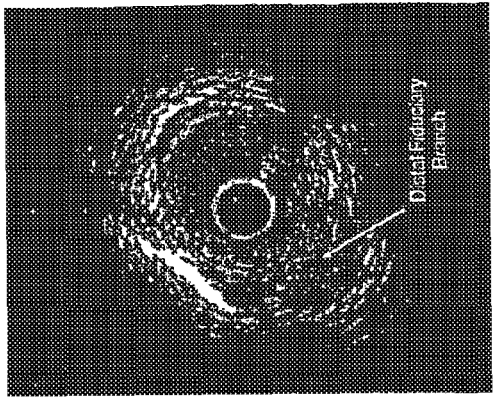
Figure 2C:
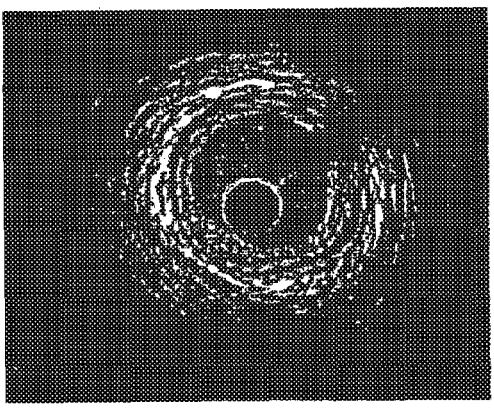
Figure 2B:
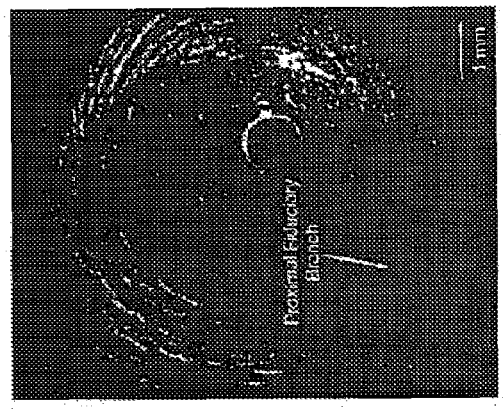

FIG. 1 provides the acute effect of a single dose of ETC-216 on serum HDL in normal male subjects;

FIG. 2(A) provides a motorized pullback of the IVUS imaging catheter beginning at a distal fiduciary branch (site C) and ending at a proximal branch (site A). The pathway of the catheter is illustrated in the angiogram;

FIG. 2(B) provides a representative cross-section of the vessel obtained every 0.5 mm until a proximal branch is reached;

FIG. 2(C) provides an intermediate cross-section of the vessel;

FIG. 2(D) provides the distal branch in the IVUS image;

FIG. 3(A) provides a cross-section for analysis;

FIG. 3(B) provides the external elastic membrane (EEM);

FIG. 3(C) provides the lumen area;

FIG. 3(D) provides the calculation of the maximal atheroma thickness measured by subtraction of the cross-sectional area of the lumen from the area of the EEM;

FIG. 4(A) provides a baseline image of a vessel in a patient before receiving ETC-216; and FIG. 4(B) provides a follow-up image of a vessel in a patient after receiving ETC-216. The atheroma area decreased from 8.1 to 5.35 mm$^3$ with virtually no change in the lumen area.

Figure 5:
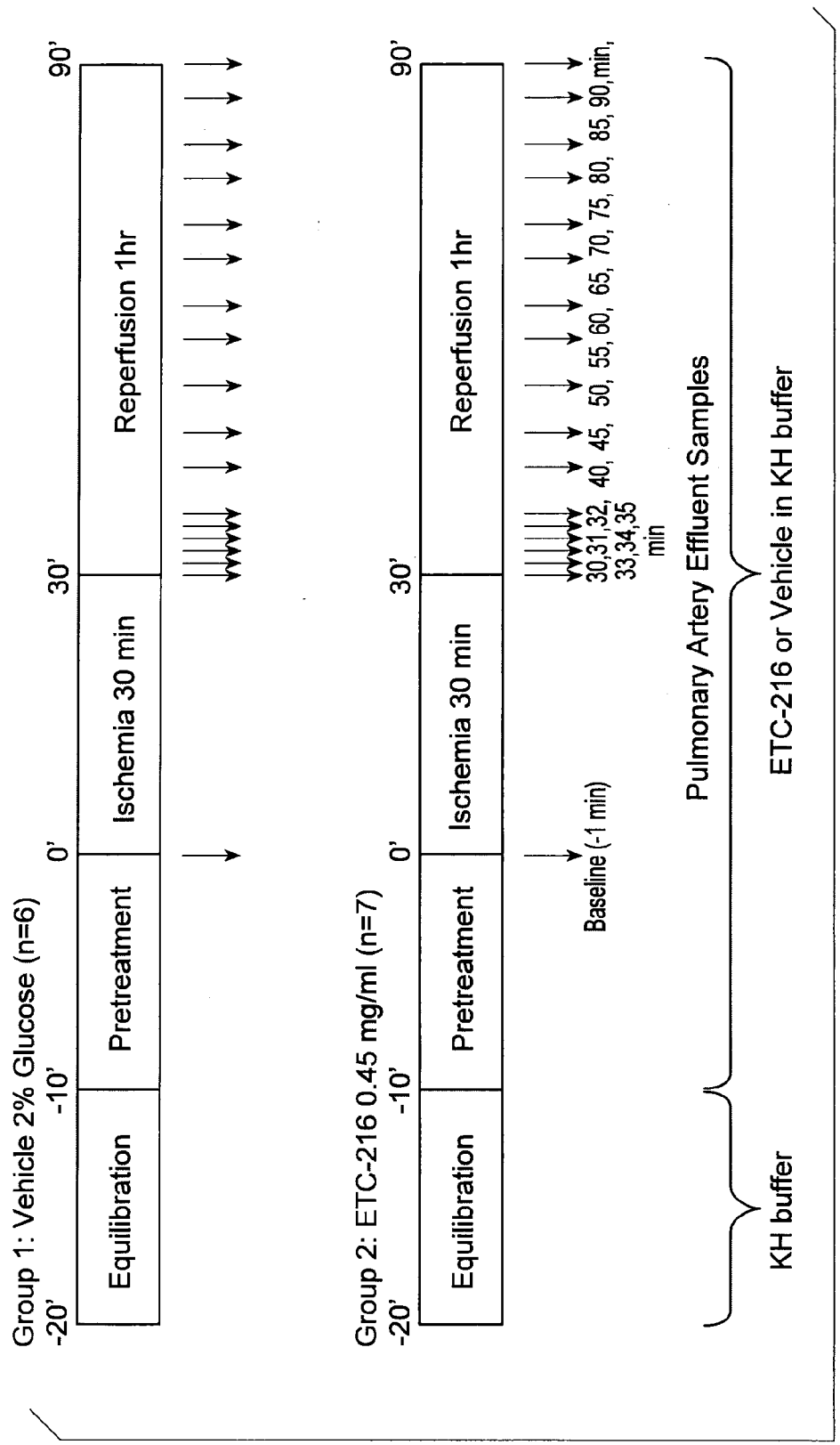
Figure 6:
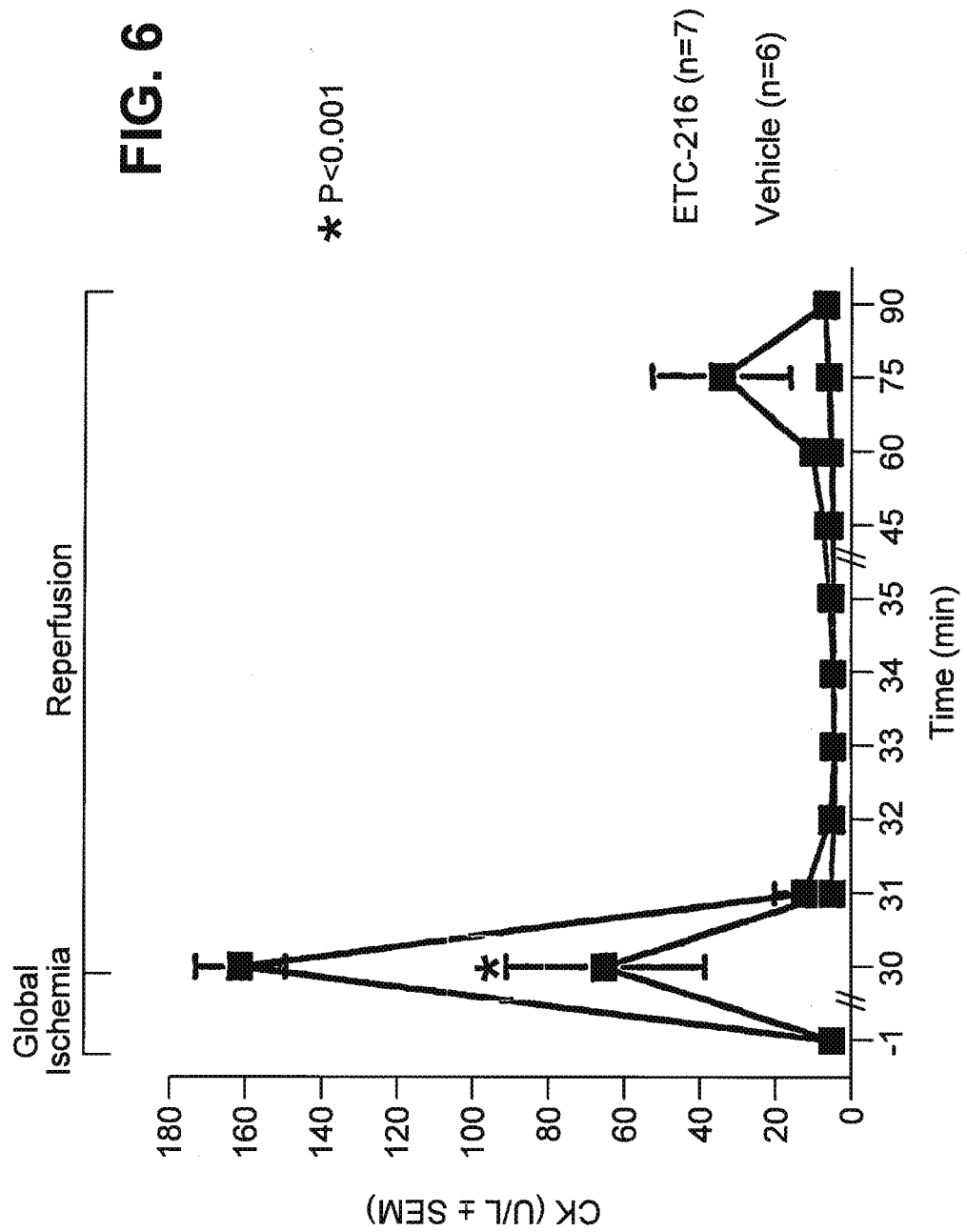
Figure 7:
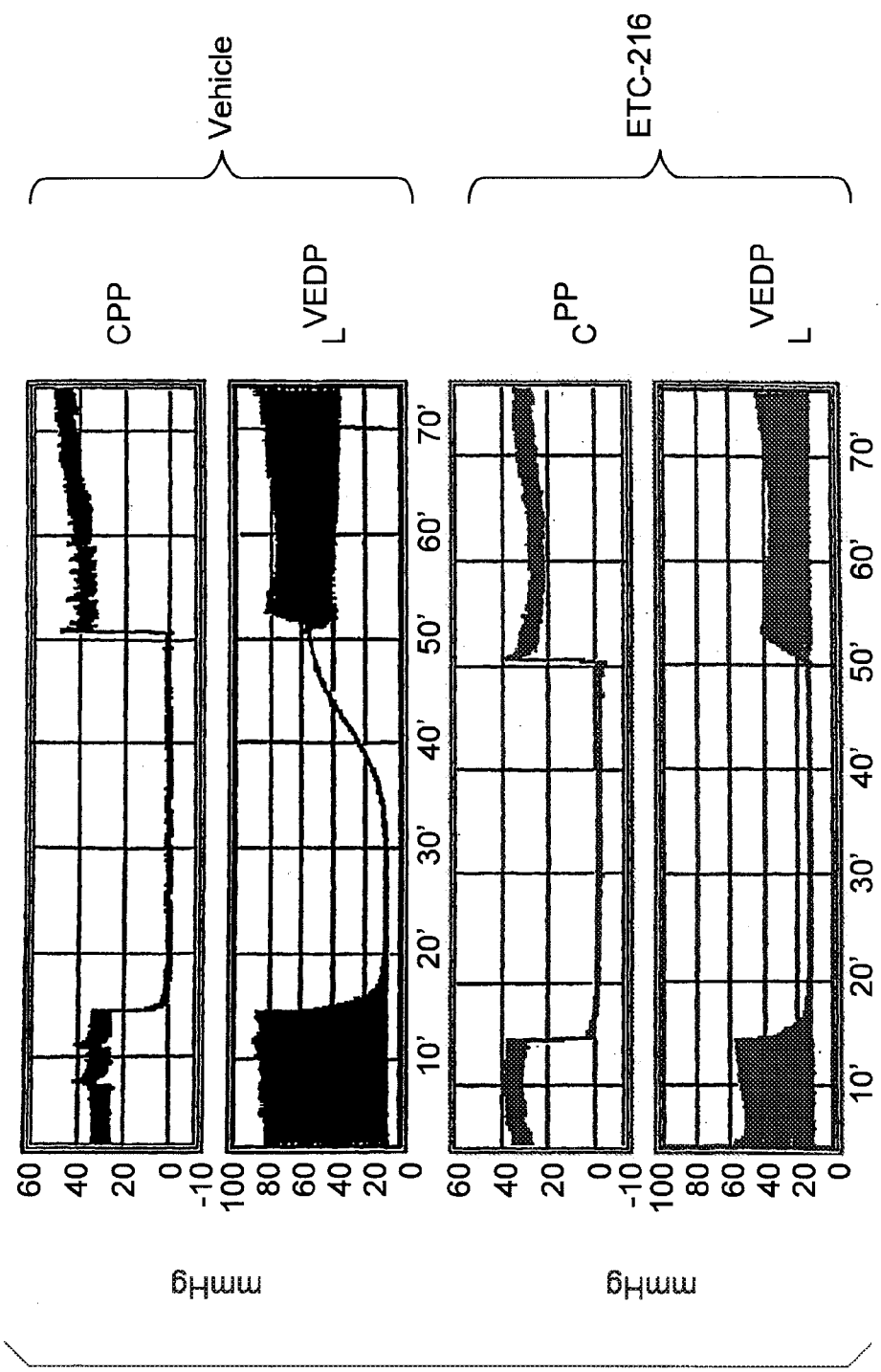
Figure 8:
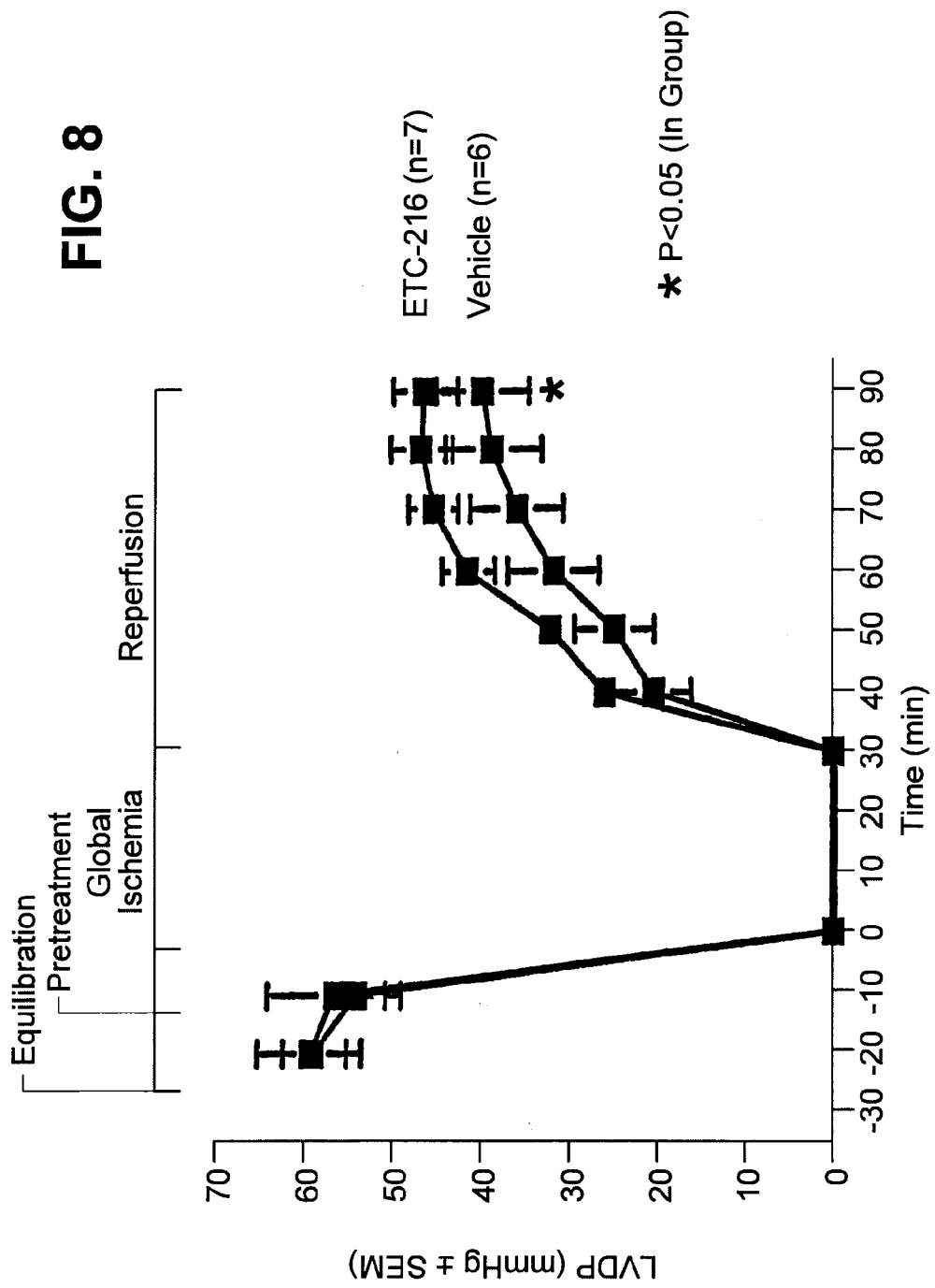
Figure 9:
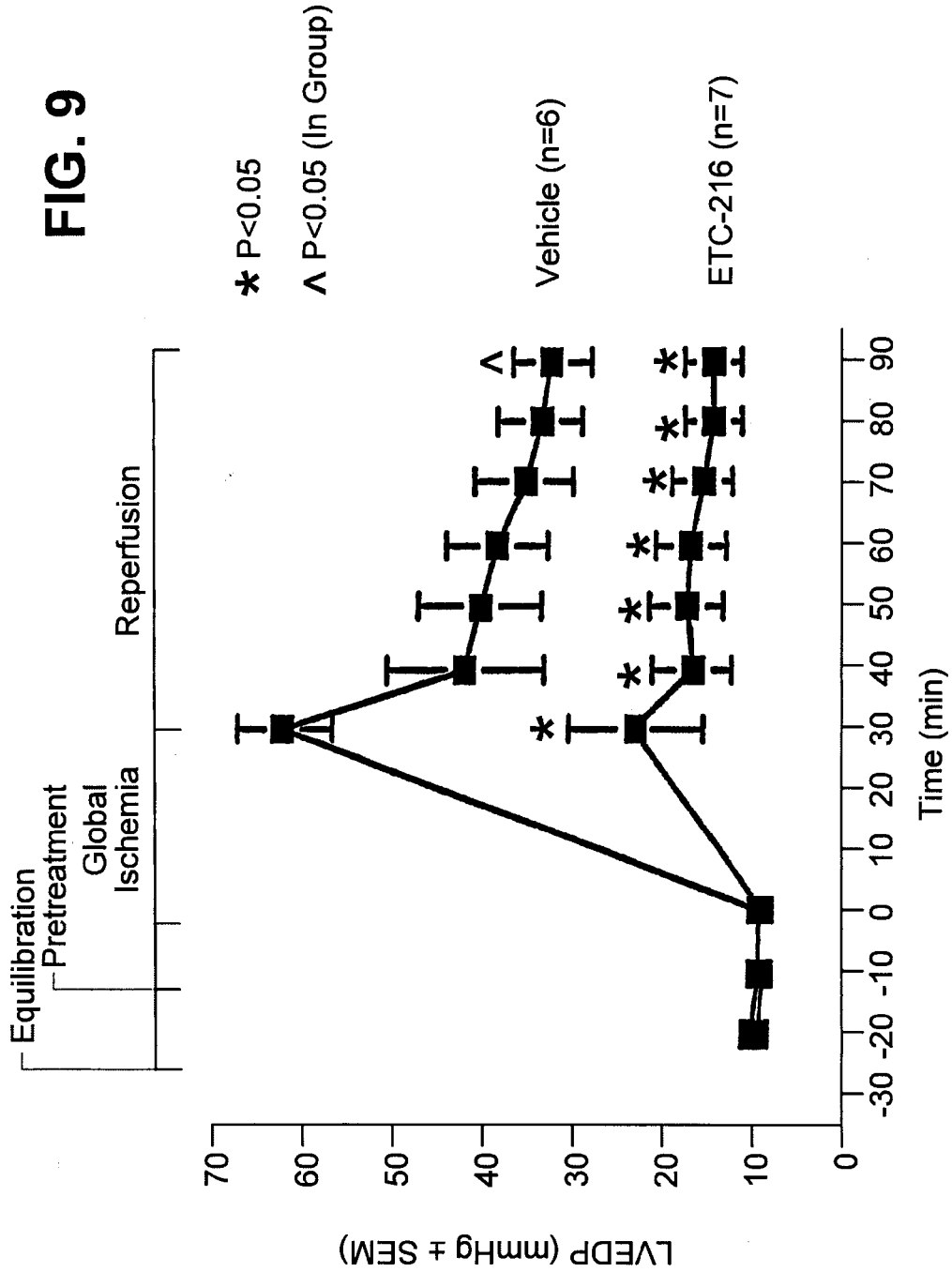
Figure 10:
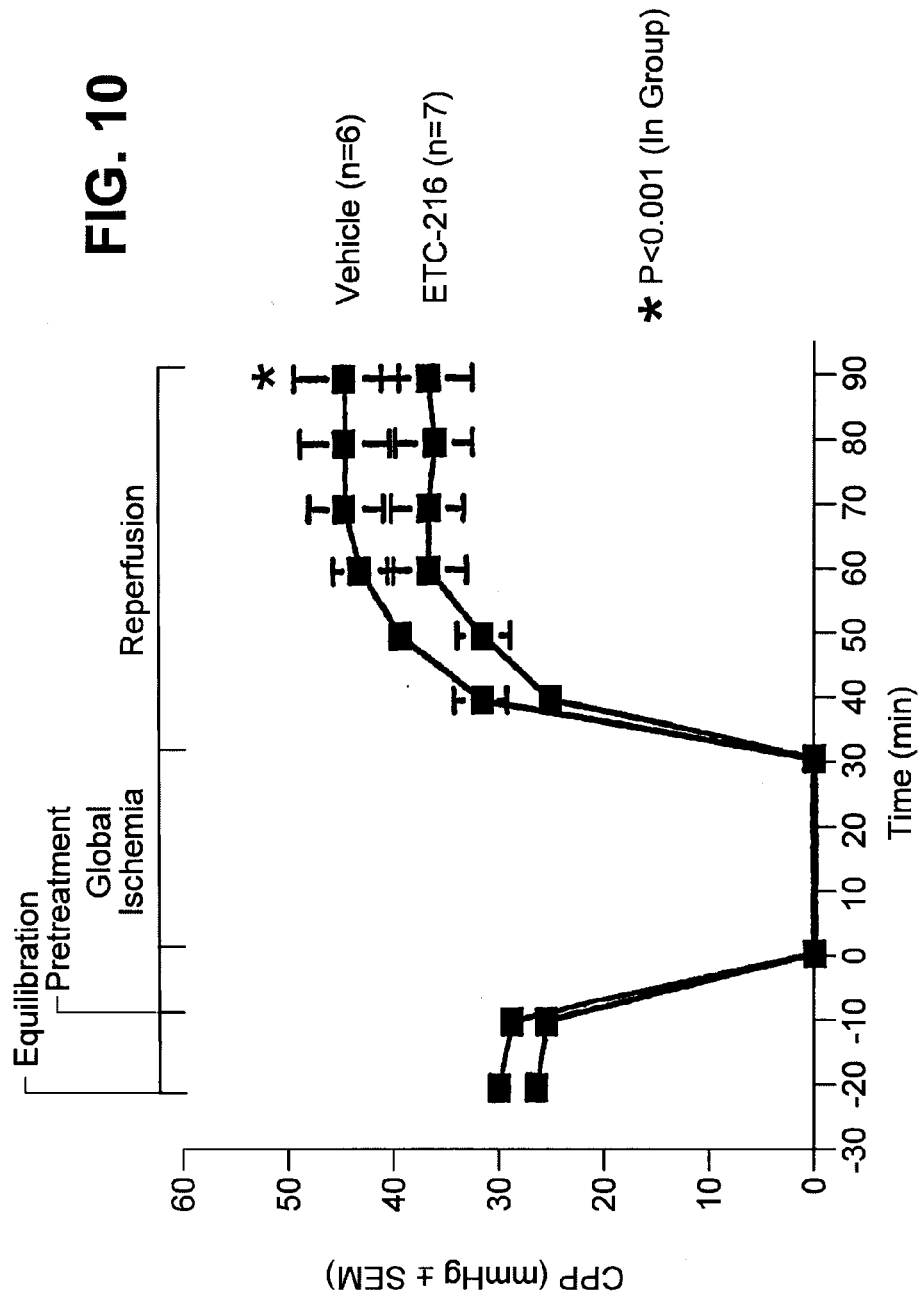
Figure 11:
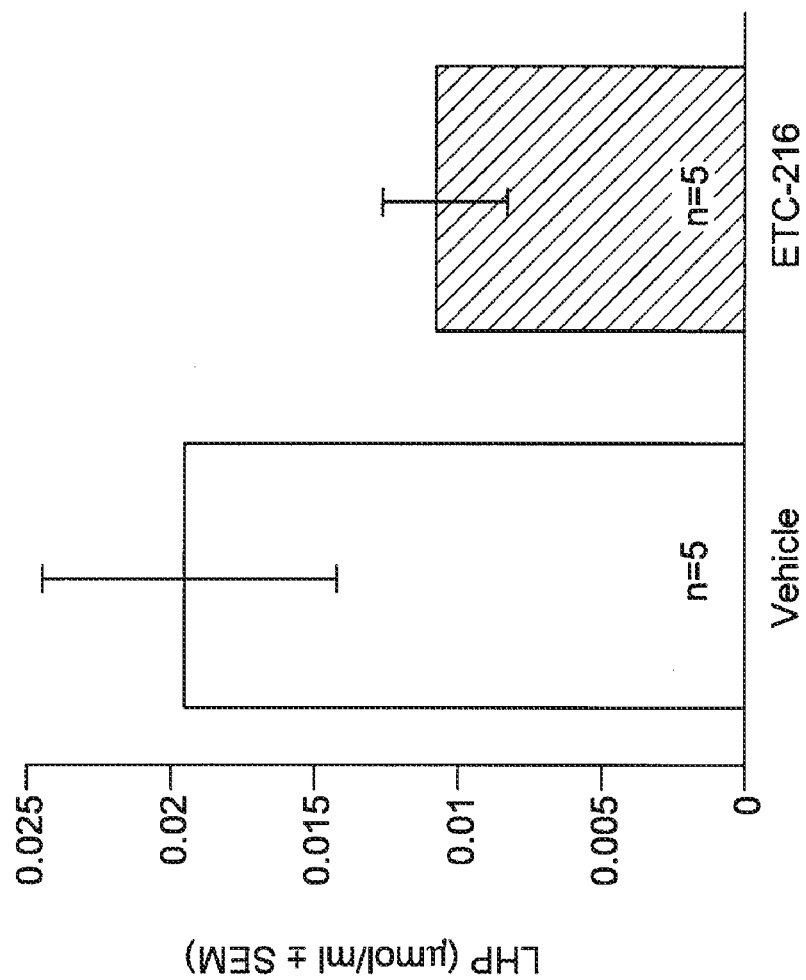
Figure 14:
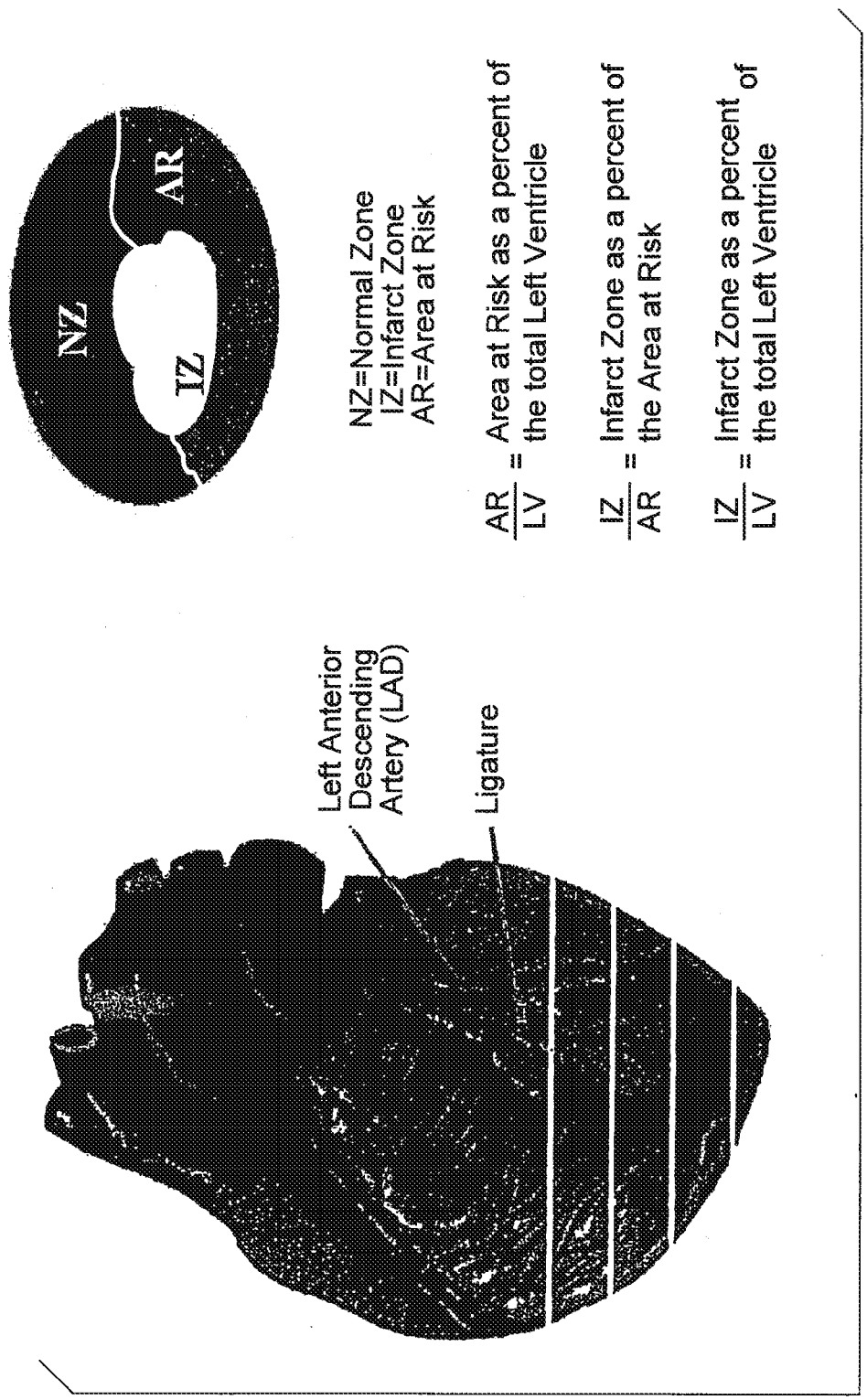
Figure 15:
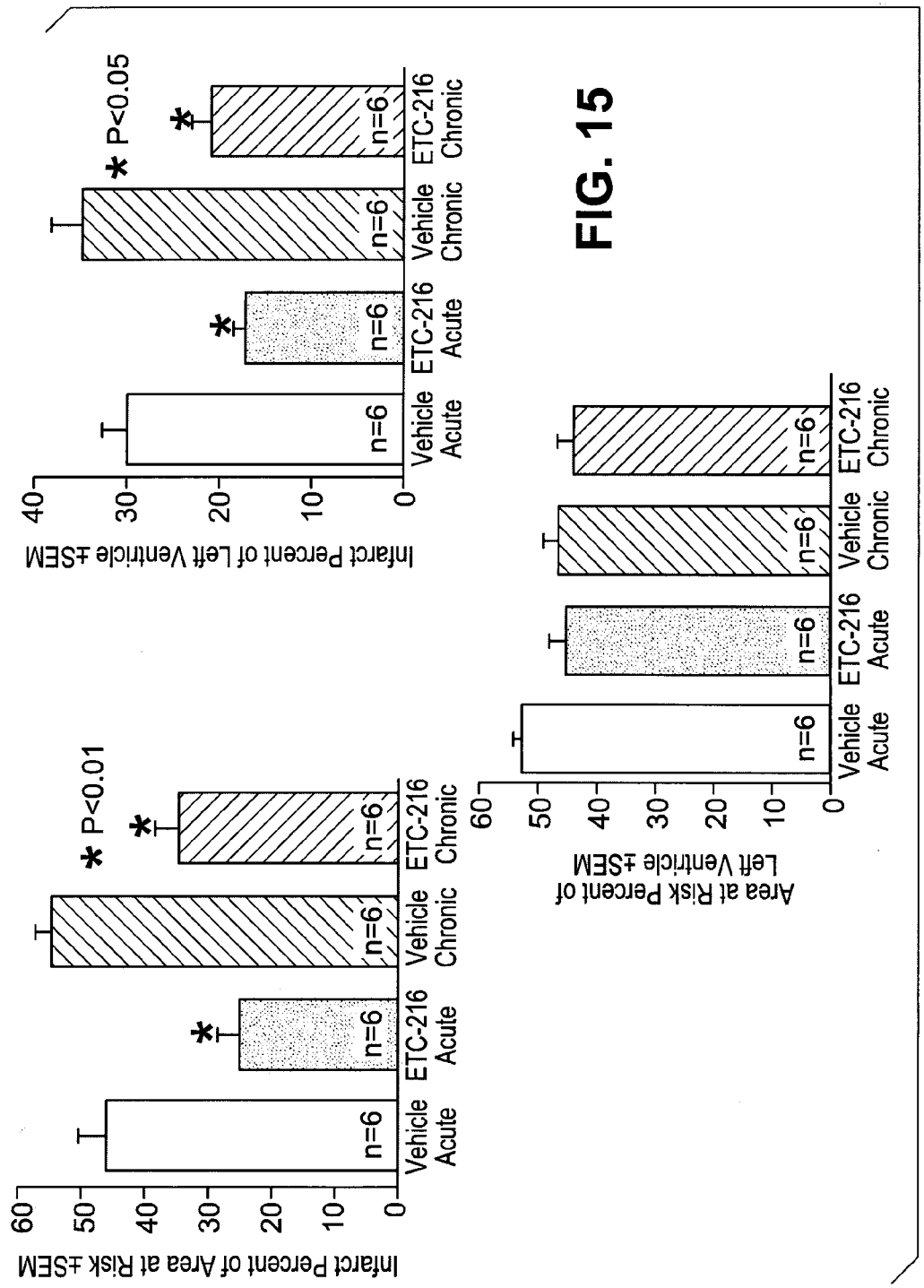
Figure 16:
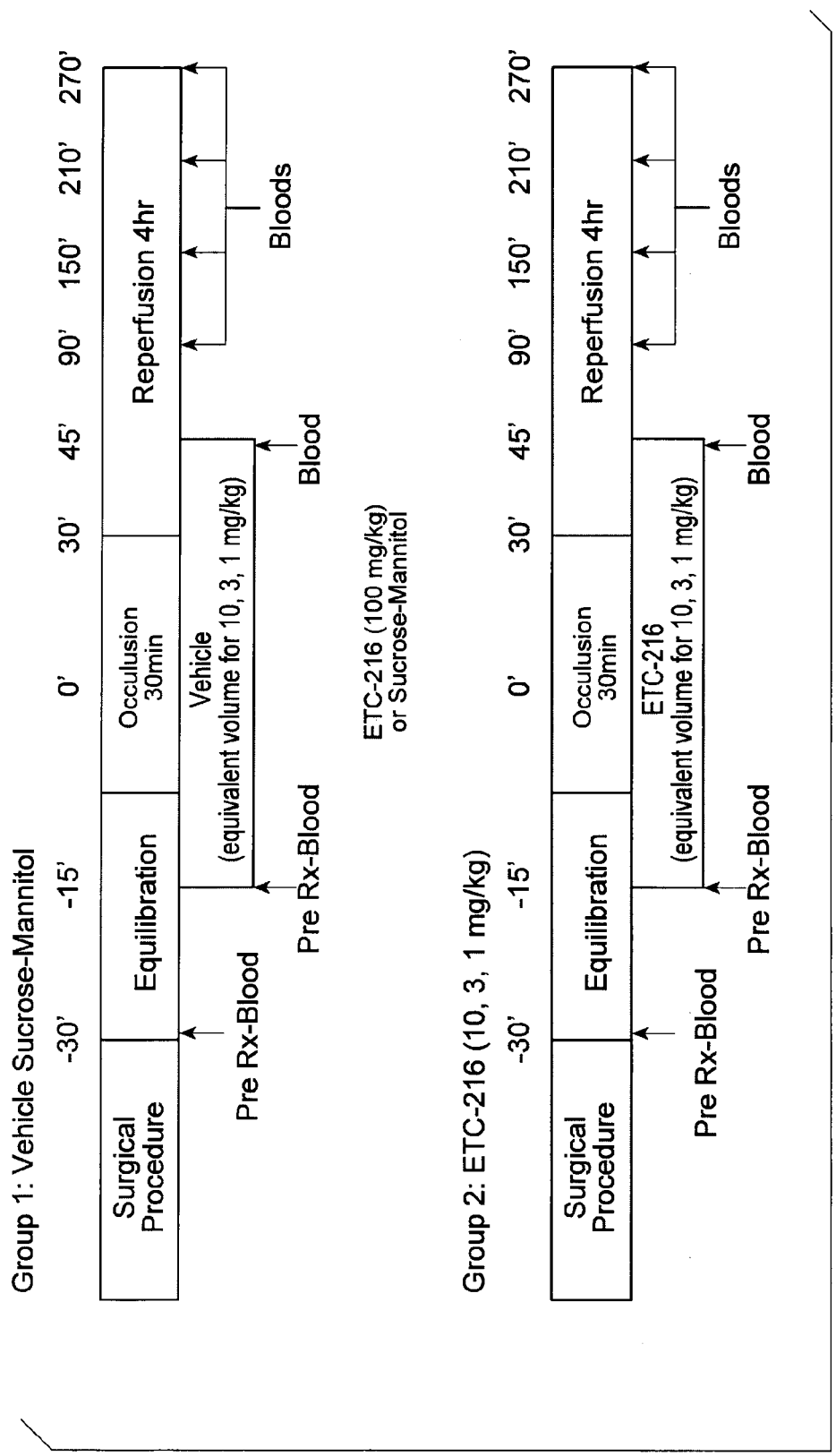
Figure 17:
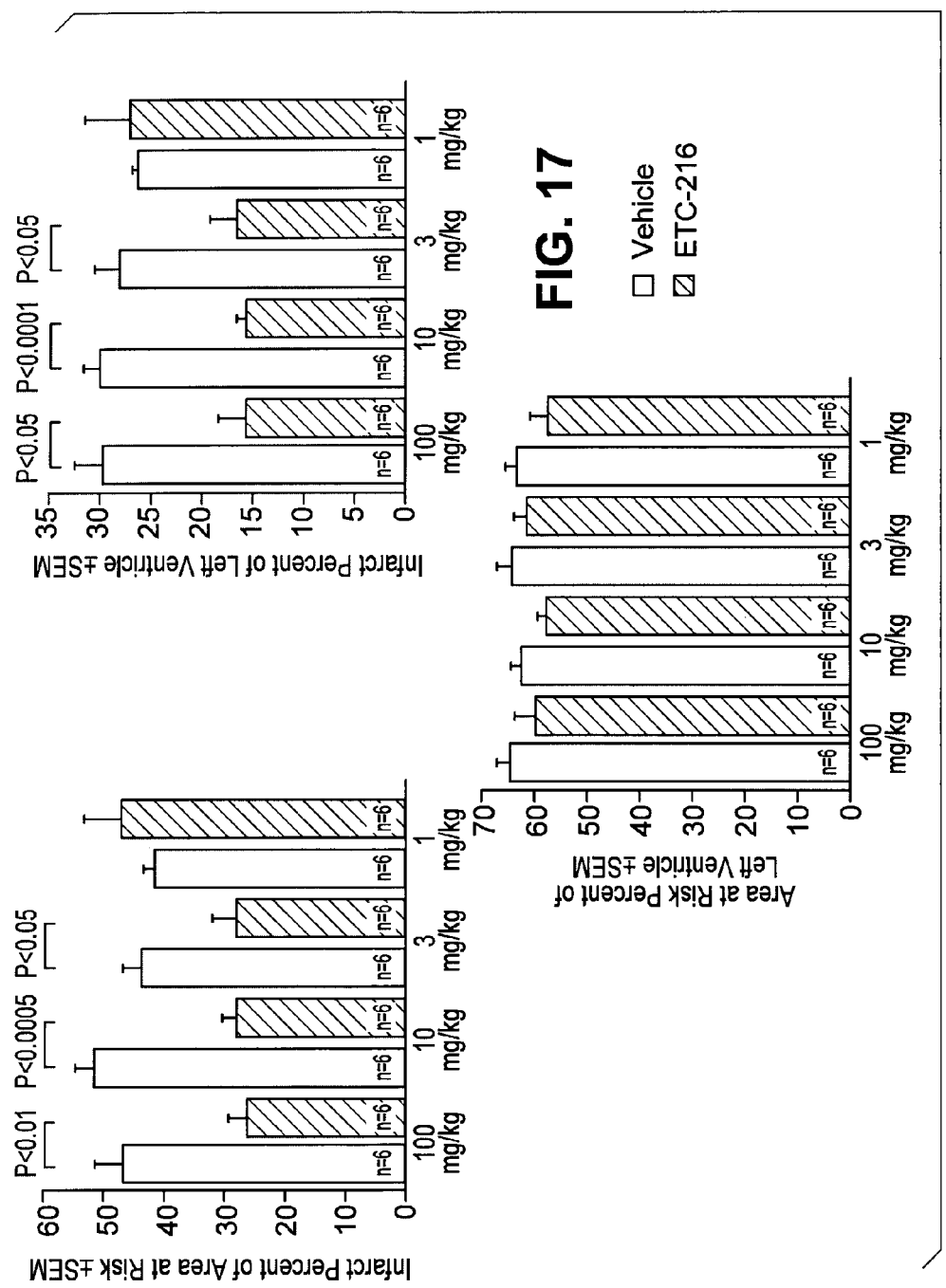
Figure 18:
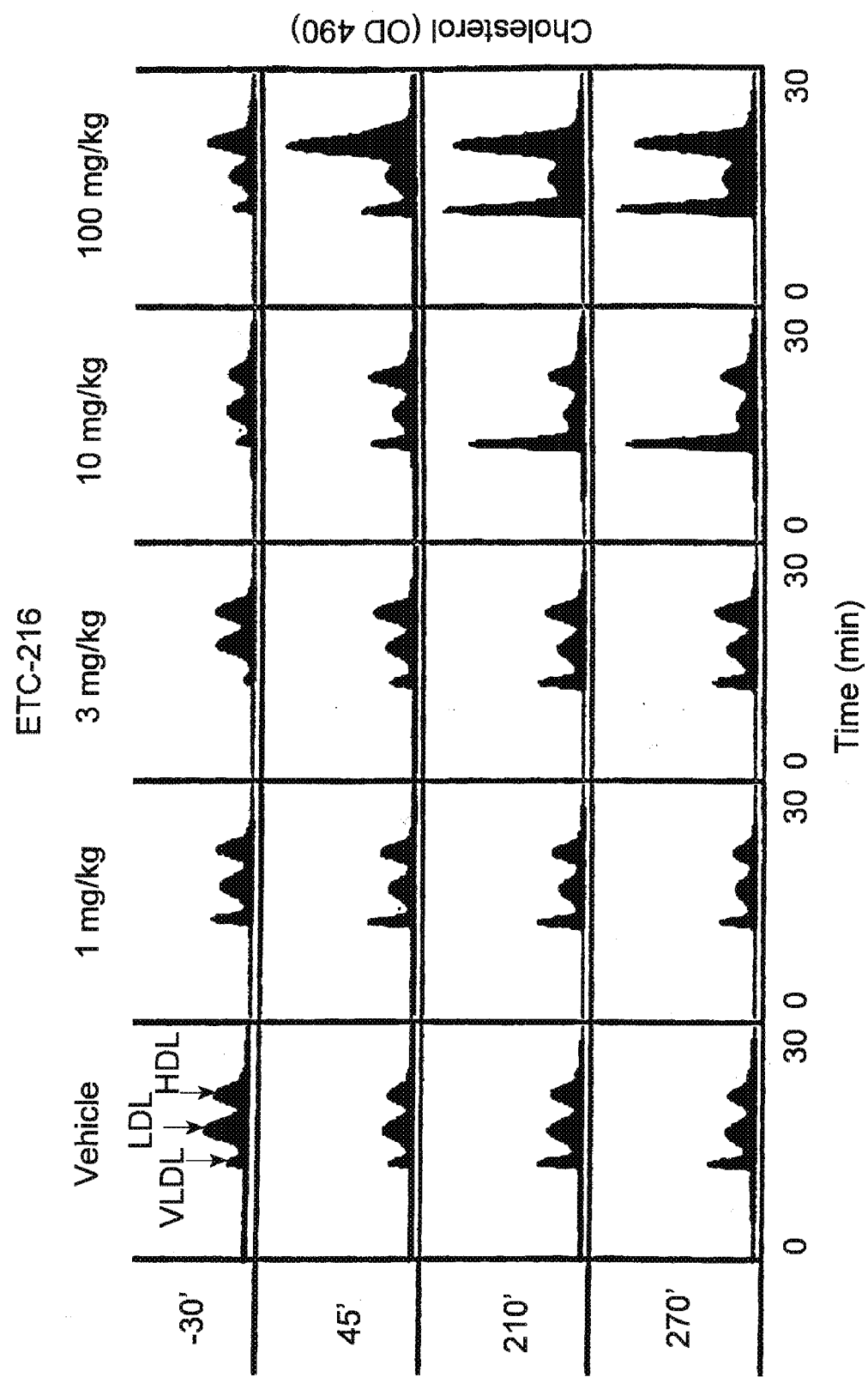
Figure 19:
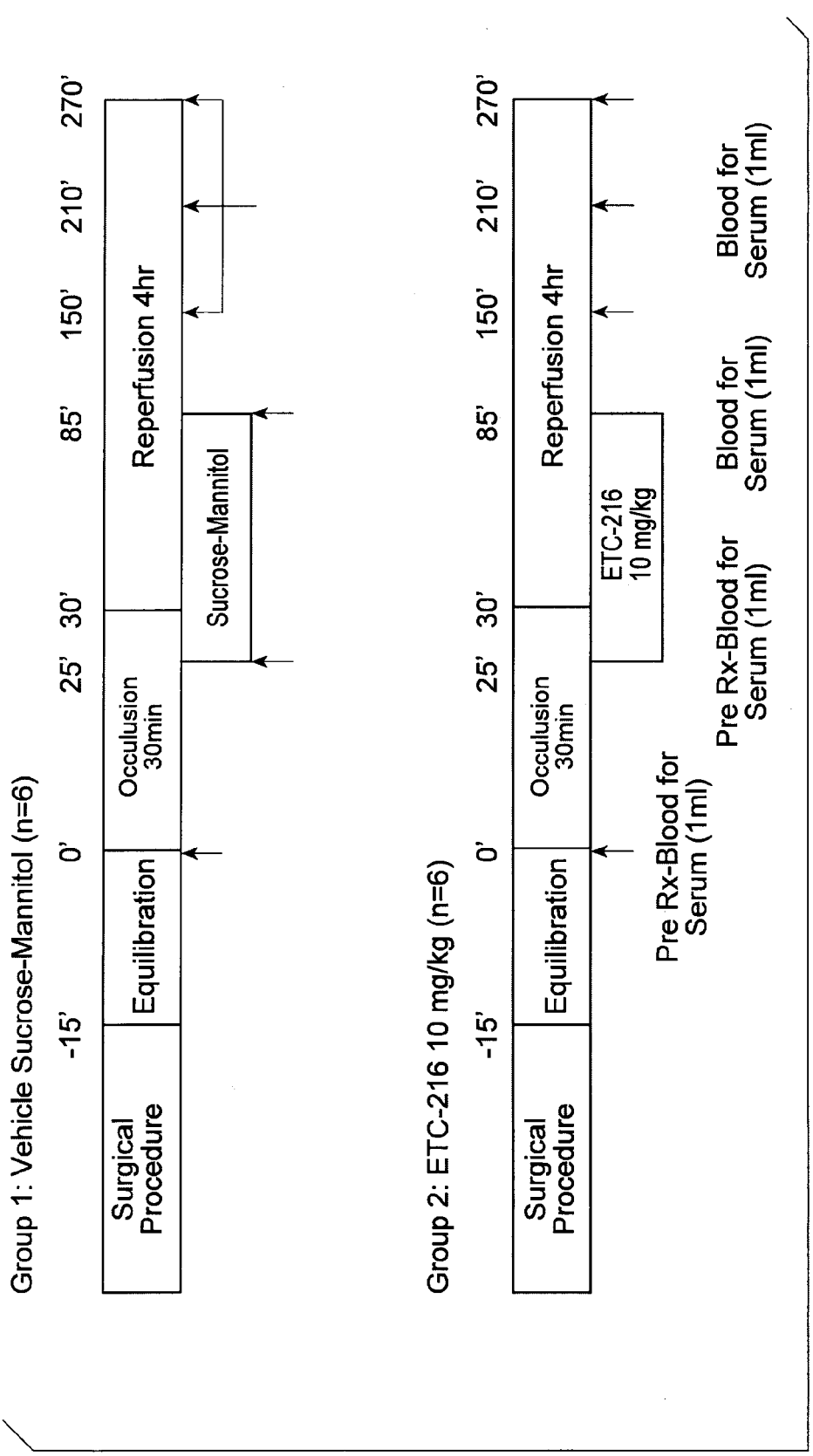
Figure 20:
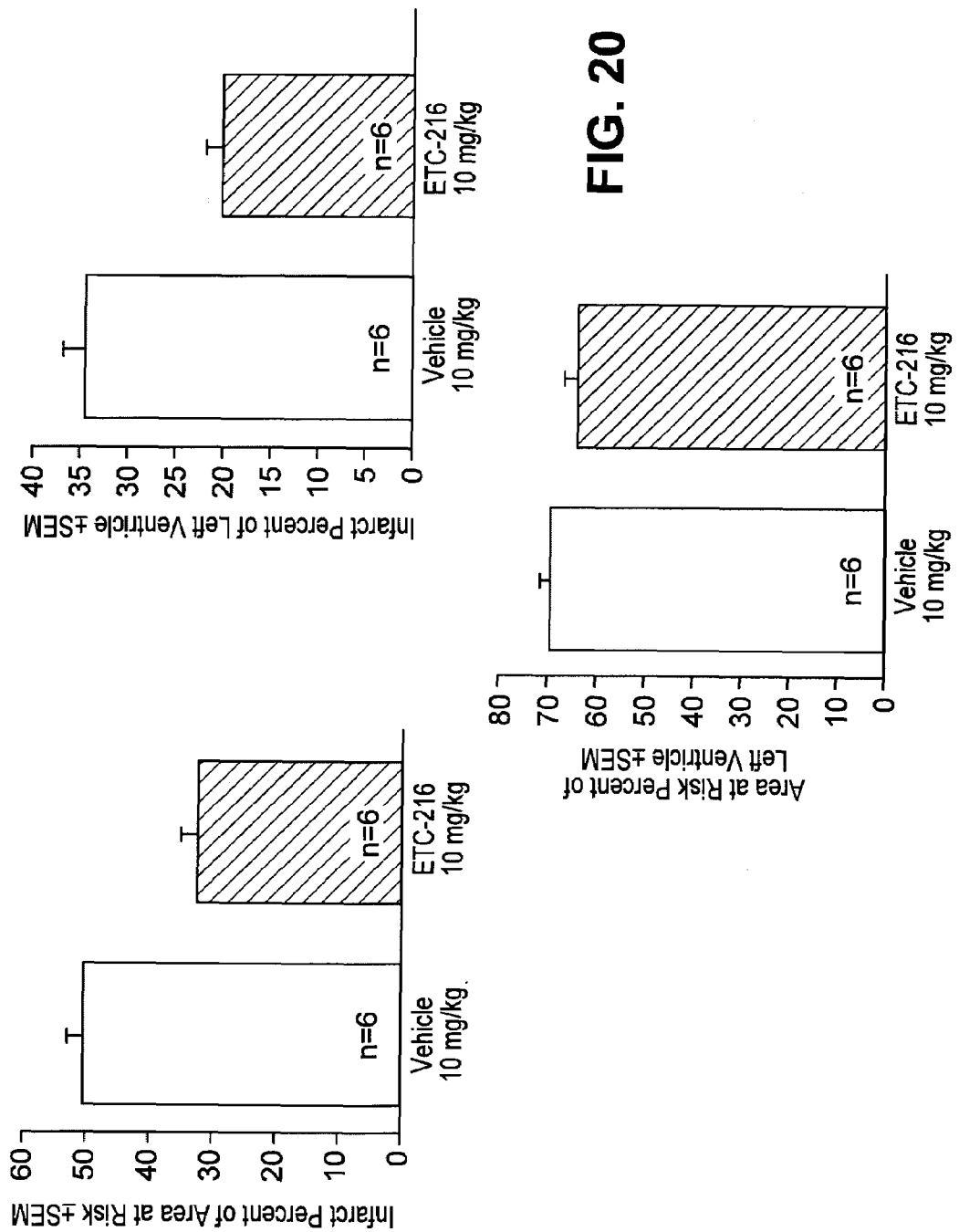

FIG. 5 provides an example of a protocol wherein isolated rabbit hearts were treated with vehicle or a protein/lipid complex of the invention (ETC-216) prior to the onset of ischemia;

FIG. 6 provides creatine kinase activity in coronary venous effluent;

FIG. 7 provides real-time monitoring of cardiac function collected from a vehicle and an ETC-216 treated isolated rabbit heart in the Langendorff Apparatus;

FIG. 8 provides the temporal changes in left ventricular developed pressure (LVDP) in isolated rabbit hearts before, during and after 30 minutes of global ischemic arrest and 60 minutes of reperfusion;

FIG. 9 provides temporal changes in left ventricular end-diastolic pressure (LVEDP) in isolated rabbit hearts before, during and after 30 minutes of global ischemic arrest and 60 minutes of reperfusion;

FIG. 10 provides temporal changes in coronary perfusion pressure (CPP) in isolated rabbit hearts before, during and after 30 minutes of global ischemic arrest and 60 minutes of reperfusion;

FIG. 11 provides lipid hydroperoxide content in tissue homogenates from vehicle and ETC-216 treated rabbit hearts subjected to global ischemic arrest for 30 minutes followed by 60 minutes reperfusion;

FIG. 12 provides electron microscope images of cardiac muscle samples from vehicle and ETC-216 treated rabbit hearts;

FIG. 13 provides an additional protocol of the present invention wherein one pretreatment was administered prior to the onset of ischemia in the acute administration group and two pretreatments were administered prior to the onset of ischemia in the chronic administration group;

FIG. 14 provides a protocol for determination of infarct size;

FIG. 15 provides infarct percent of area at risk, infarct percent of left ventricle, and area at risk percent of left ventricle in rabbits treated once (i.e., acute treatment) or treated twice (i.e., chronic treatment) with ETC-216 (100 mg/kg) or an equivalent volume of vehicle;

FIG. 16 provides an additional protocol of the present invention wherein rabbits were pretreated prior to the onset of ischemia with either vehicle (Group 1) or 10, 3 or 1 mg/kg of ETC-216 (Group 2);

FIG. 17 provides infarct percent of area at risk, infarct percent of left ventricle, and area at risk percent of left ventricle determined in rabbits treated once (i.e., acute treatment) with 10, 3 or 1 mg/kg of ETC-216 or with an equivalent volume of sucrose-mannitol vehicle for each group;

FIG. 18 provides temporal changes in lipoprotein unesterified cholesterol;

FIG. 19 provides an additional protocol of the present invention wherein a single treatment of vehicle of ETC-216 was administered during the last 5 minutes of the 30 minute ischemic period; and FIG. 20 provides infarct percent of area at risk, infarct percent of left ventricle, and area at risk percent of left ventricle determined in rabbits.

5. DETAILED DESCRIPTION OF THE INVENTION

5.1. Definitions

As used herein, the following terms shall have the following meaning:

The terms "treat", "treating" or "treatment" refer to a method of alleviating or abrogating a disease, disorder and/or symptoms thereof.

The term "therapeutically effective amount" refers to that amount of Apo A-I Milano or lipid complex or pharmaceutical formulation thereof sufficient to alleviate to some extent one or more of the symptoms of the condition or disorder being treated.

The terms "prevent", "preventing" or "prevention" refer to a method of barring a subject from acquiring a disease, disorder and/or symptoms thereof. In certain embodiments, the terms "prevent", "preventing" or "prevention" refer to a method of reducing the risk of acquiring a disease, disorder and/or symptoms thereof.

The term "prophylactically effective amount" refers to that amount of the Apo A-I Milano or lipid complex or pharmaceutical formulation thereof sufficient to result in the prevention, onset or recurrence of one or more symptoms of the condition or disorder being treated.

The term "acute coronary syndromes" refers to ischemic disorders such as unstable angina, Q wave and non-Q wave myocardial infarction or as provided by International Classification of Disease 9$^{th}$ version (ICD-9) to be superceded by 10$^{th}$ version (ICD-10). The myocardial infarction can present with or without an ST-segment elevation on electrocardiograph.

The term "ischemia" refers to local anemia due to mechanical or biologically induced, e.g., spasm, thrombosis, stenosis obstruction (mainly arterial narrowing or disruption) of the blood supply. The term "myocardial ischemia" refers to inadequate circulation of blood to the myocardium, usually as a result of coronary artery disease.

The term "ischemic reperfusion" refers to reestablishment of an increased amount of oxygenated blood to the tissue.

The term "cardiovascular diseases" refers to the heart, the blood vessels and the blood circulation diseases such as myocardial infarction, acute coronary syndrome, atherosclerosis, angina, ischemic reperfusion injury and related disorders.

The term "surgical intervention" as used herein refers to manual, non pharmacologic or operative methods. Surgical intervention can be for diagnostic, radiologic, prophylactic or treatment purposes.

The term "unstable angina" refers to a change in frequency, severity or duration of symptoms of chronic stable angina, such as pain in the chest that can radiate to the jaws and arms or epigastric pain. Chronic stable angina is pain in the chest, which can radiate to the jaws and arms of a subject that is induced by exercise, eating and/or stress and is relieved by rest without recent change in frequency or severity of activity necessary to produce symptoms.

The term "pharmaceutical formulation" refers either to a composition comprising Apo A-I Milano or an Apo A-I Milano:lipid complex and a suitable diluent, carrier, vehicle, or excipients suitable for administration to a subject. This term includes, but is not limited to oral, parenteral and topical compositions as described below.

The term "about" refers to a relative term denoting an approximation of plus or minus 20% of the nominal value it refers to. For the field of this disclosure, this level of approximation is appropriate unless the value is specifically stated require a tighter range.

The term "label" refers to a display of written, printed or graphic matter upon the immediate container of an article, for example, the written material displayed on a vial containing a pharmaceutically active agent.

The term "labeling" refers to all labels and other written, printed or graphic matter upon any article or any of its containers or wrappers or accompanying such article, for example, a package insert, instructional videotapes or instructional DVDs accompanying or associated with a container of a pharmaceutically active agent.

5.2. Methods of Treatment

The invention provides methods and formulations for the treatment or prevention of acute coronary syndromes, including unstable angina, ST-segment elevation myocardial infarction and non Q wave myocardial infarction. Safe and effective doses for the pharmaceutical formulations described herein have been determined by Applicants for the treatment and prevention of acute coronary syndromes.

Based on current understanding, a framework has emerged which has reorganized clinical presentations, now termed acute coronary syndromes ("ACS"). Id. Acute coronary syndromes comprises unstable angina, Q wave and non-ST-segment elevation myocardial infarction and is a major cause of morbidity and mortality, especially within the first 24 hours after presentation. (Schoenhagen et al., 2000, *Circulation* 101: 598-603). ACS is an ischemic discomfort that presents without ST segment elevation on an electrocardiograph. The ischemia often develops into unstable angina, Q wave and non-Q wave myocardial infarction. (Antman and Braunwald, "Acute Myocardial Infarction" in Heart Disease, A Textbook of Cardiovascular Medicine, 6$^{th}$ edition, vol. 2, Braunwald et al., eds, 2001, W. B. Saunders Company, Philadelphia).

The methods and formulations of the invention provide unique and effective approach to the treatment of atherosclerosis and acute coronary syndromes. In the methods of the invention, Apo A-I Milano:phospholipid complexes or pharmaceutical formulations thereof provide a non-surgical therapy that reverses the pathophysiologic basis of the disease rather than provide symptomatic relief. The methods of the invention provide administration of Apo A-I Milano, Apo A-I Milano:phospholipid complex or pharmaceutical formulations thereof that provide HDL therapy which promotes cholesterol efflux, reverse cholesterol transport and reduces atherosclerotic plaque. Without being bound to any theory, it is believed the Apo A-I Milano, Apo A-I Milano:phospholipid complex or pharmaceutical formulations thereof mimic a functional HDL that promotes cholesterol efflux and reverse cholesterol transport, reduces atheroma volume and can stabilize atherosclerotic plaque.

The invention provides methods for the treatment of acute coronary syndromes. In preferred embodiments, Apo A-I Milano:phospholipid complexes or pharmaceutical formulations thereof, as described below, can be administered in a dose of about 1 mg (protein)/kg to about 100 mg (protein)/kg preferably a dose of 1 mg (protein)/kg to 50 mg (protein)/kg; most preferably, 15 mg/kg or 45 mg/kg. Applicants have shown that the these doses are safe, effective and well tolerated by subjects suffering from or at risk for acute coronary syndromes as described in detail herein.

The invention provides methods for the treatment or prevention of acute coronary syndromes including alleviation or amelioration of the signs or symptoms of acute coronary syndromes. In certain embodiments, the methods provide for the treatment or reduction of coronary atherosclerosis. In certain embodiments, the methods provide for the promotion of cholesterol efflux from affected vessels. In certain embodiments, the methods provide for the promotion of reverse cholesterol transport. In one embodiment, the methods provide for decreased atheroma volume in an affected vessel. In certain embodiments, the affected vessel is a coronary artery. Atheroma volume can be determined, as described herein, by intravascular ultrasound (IVUS). In certain embodiments, the methods provide for a decrease in total plaque volume of an affected vessel. In certain embodiments, the methods provide for a decrease in the average maximal plaque thickness in an affected vessel. In certain embodiments, the methods provide for a decrease in average maximal atheroma thickness. In certain embodiments, the methods provide for a decrease in plaque volume in least percent plaque area. In certain embodiments, the methods provide for a decrease in the greatest percent plaque area. In certain embodiments, the methods provide for increased mean coronary luminal diameter in an affected vessel. In certain embodiments, the subject receiving the methods and formulations of the invention, can have decreased angiographic lesions as compared with subjects not receiving the methods and formulations of the invention. In certain embodiments, the methods provide a regression in pre-existing lesions. In certain embodiments, the methods and pharmaceutical formulation provide for achieving patency of an occluded vessel or maintaining patency of an occluded vessel.

In certain embodiments, doses the Apo A-I Milano:phospholipid complex of about 15 mg/kg to about 45 mg/kg provide for the mean percent atheroma volume reduction of about 2%, about 1% or about 0.05%. In certain embodiments doses the Apo A-I Milano:phospholipid complex of about 15 mg/kg to about 45 mg/kg provide for a reduction in atheroma volume of about 20 mm$^3$, about 15 mm$^3$, about 10 mm$^3$ or about 5 mm$^3$. In certain embodiments doses the Apo A-I Milano:phospholipid complex of about 15 mg/kg to about 45 mg/kg provide for the reduction in mean maximum atheroma thickness by about −0.039 mm to −0.044 mm.

In one embodiment, the methods provide for the treatment of acute coronary syndromes in subjects with signs or symptoms of acute coronary syndromes. In one embodiment, subjects can have signs and/or symptoms of myocardial ischemia, for instance, pain in the chest, jaw, arms, or epigastric region, palpitations, shortness of breath, diaphoresis, nausea and/or vomiting. In another embodiment, the methods provide for treatment of acute coronary syndromes in subjects exhibiting signs and symptoms of acute coronary syndromes in conjunction with changes in electrocardiogram ("ECG" or "EKG"), such as ST segment elevations, T wave changes such as inversions, increases in creatine kinase fraction, troponin I or C-reactive protein.

In one embodiment, the methods provide for prevention of acute coronary syndromes in subjects at risk for developing acute coronary syndromes. Subjects at risk can include, subjects of varying ages (for example, 18-24, about 25, about 30, about 40, about 50, about 60, about 70, about 80 or about 90 years of age), subjects with a family history of cardiovascular disease or genetic predisposition to cardiovascular disease, subjects that have diabetes, hypertension, multiple-vessel or left-mainstem disease or have had a previous myocardial infarction.

It is understood by those of skill in the art that the actual dose of the formulations of the invention can vary with the height, weight, age, severity of illness of the subject, the presence of concomitant medical conditions and the like. For example, an elderly subject with compromised renal or liver function can be treated with a dose of Apo A-I Milano:lipid complex that is at the lower range of the about 1 mg/kg dose (e.g., 0.8 mg/kg or 0.9 mg/kg). A subject with severe acute coronary syndromes that is obese with good renal and liver function can be treated with a dose of Apo A-I Milano:lipid complex that is, for example, at the upper range of the about 100 mg/kg dose (e.g., 120 mg/kg, 119 mg/kg, 118 mg/kg, 115 mg/kg and the like). The dosage of the formulations described herein have been shown to be effective to achieve the intended purpose. These doses achieve a range of circulating concentrations that include the effective dose with an acceptable risk to benefit profile.

The invention provides methods of treating or preventing acute coronary syndromes with a dosing administration schedule sufficient to treat acute coronary syndromes in a subject in need of such treatment. In certain embodiments, the Apo A-I Milano:phospholipid complex or pharmaceutical formulation thereof, as described below, can be administered about every day, about every other day, about every 3 days, about every 4 days, about every 5 days, about every 6 days, about every 7 days, about every 8-10 days or about every 11-14 days. This time period is also referred to as the dosing interval or interval. In certain embodiments the dosing interval can be every month, every six months, every 12 months, every 18 months or every 24 months. In preferred embodiments, the Apo A-I Milano, lipid complex or pharmaceutical formulation thereof can be administered about every 7 days. In certain embodiments, administration of Apo A-I Milano: phospholipid complexes or pharmaceutical formulations thereof can be a one time administration. In certain embodiments, administration can continue for about 1 week, about 2 weeks, about 3 weeks, about 4 weeks, about 5 weeks, about 6 weeks, about 7-12 weeks, about 13-24 weeks, about 52 weeks or continued for the life of the subject. This time period is also referred to as the dosing duration, treatment duration or duration. Thus, a dosing administration schedule can be, for example, a pharmaceutical formulation of an Apo A-I Milano:phospholipid complex administered about every 7 days for about 6 weeks. In certain embodiments, the dosing interval can continue intermittently after about 52 weeks. For example, a subject can be treated once a week for about 52 weeks and then treated about 3 to about 4 times over the following year. In certain preferred embodiments, administration of a pharmaceutical formulation comprising Apo A-I Milano:phospholipid complex is about every 7 days for about 5 weeks. Other dosing administration schedules using various dosing intervals and durations are within the scope of the invention as described herein.

The dose of Apo A-I Milano:phospholipid complex or pharmaceutical formulations thereof can vary over the duration of treatment. For example, a subject can be treated with 45 mg/kg of a pharmaceutical formulation of an Apo A-I Milano:phospholipid complex once weekly for 3 weeks and then treated with 15 mg/kg of a pharmaceutical formulation of an Apo A-I Milano:phospholipid complex once every four months or once per year for the lifetime of the subject. Such intermittent doses can be administered to maintain the patency of a vessel. Intermittent doses during the lifetime of the subject to maintain a reduced atheroma volume and increased vessel lumen are within the scope of the invention.

The methods and formulations of the present invention can be used in conjunction with surgical intervention, i.e., before, during or after surgery. Surgical intervention can include angioplasty, intravascular ultrasound, coronary artery bypass graft (CABG), coronary angiography, implantation of vascular stents, percutaneous coronary intervention (PCI) and/or stabilization of plaques. In certain embodiments, the methods provide for dosing of Apo A-I Milano:phospholipid complex or pharmaceutical formulations thereof before or after surgical intervention to open an occluded vessel, or reduce atherosclerotic plaque in a vessel. Surgical intervention refers to manual, non-pharmacologic or operative methods used for diagnosis, imaging (radiology) prevent or treatment of disease or a condition. For example, intravascular ultrasound (IVUS) and coronary angiography are procedures that can provide a quantitative assessment of plaque burden (diagnostic purpose), angiography can provide images of vessels (radiologic purpose) and angioplasty can open an occluded vessel (treatment purpose). All are included as surgical interventions as used herein.

5.3. ApolipoproteinA-I Milano

In one aspect, the present invention provides methods and formulations for the treatment, reduction or prevention of injury from acute coronary syndromes by administering a formulation comprising Apo A-I Milano. In certain embodiments the Apo A-I Milano(Apo A-I Milano) can be complexed with a lipid.

Human Apo A-I Milano is a natural variant of Apo A-I (Weisgraber et al. 1980, *J. Clin. Invest.* 66: 901-907). In Apo A-I Milano the amino acid arginine (Arg173) is replaced by the amino acid cysteine (Cys173). Because Apo A-I Milano contains one cysteine residue per polypeptide chain, it may exist in a monomeric, homodimeric, or heterodimeric form. (see, U.S. Pat. No. 5,876,968, incorporated herein by reference in its entirety). These forms are chemically interchangeable, and the term Apo A-I Milano does not discriminate between these forms. On the DNA level the variant form results from a C to T substitution in the gene sequence, i.e. the codon CGC changed to TGC, allowing the translation of a cysteine (Cys) instead of arginine (Arg) at amino acid position 173.

In certain embodiments, the Apo A-I Milano can be a variant or conservatively substituted Apo A-I Milano. By conservative substitution it is meant that certain amino acid residues of Apo A-I Milano can be replaced with other amino acid residues without significantly deleteriously affecting the activity of the protein. Thus, also contemplated by the present invention are altered or substituted forms of Apo A-I Milano wherein at least one defined amino acid residue in the structure is substituted with another amino acid residue. For purposes of determining conservative amino acid substitutions, the amino acids can be conveniently classified into two main categories—hydrophilic and hydrophobic—depending primarily on the physical-chemical characteristics of the amino acid side chain. These two main categories can be further classified into subcategories that more distinctly define the characteristics of the amino acid side chains. For example, the class of hydrophilic amino acids can be further subdivided into acidic, basic and polar amino acids. The class of hydrophobic amino acids can be further subdivided into apolar and aromatic amino acids. The definitions of the various categories of amino acids that define structure (I) are as follows:

"Hydrophilic Amino Acid" refers to an amino acid exhibiting a hydrophobicity of less than zero according to the normalized consensus hydrophobicity scale of Eisenberg et al., 1984, *J. Mol. Biol.* 179:125-142. Genetically encoded hydrophilic amino acids include Thr (T), Ser (S), His (H), Glu (E), Asn (N), Gln (O), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include His (H), Arg (R) and Lys (K).

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Hydrophobic Amino Acid" refers to an amino acid exhibiting a hydrophobicity of greater than zero according to the normalized consensus hydrophobicity scale of Eisenberg, 1984, *J. Mol. Biol.* 179:125-142. Genetically encoded hydrophobic amino acids include Pro (P), Ile (I), Phe (F), Val (V), Leu (L), Trp (W), Met (M), Ala (A), Gly (G) and Tyr (Y).

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently (C$_1$-C$_6$) alkyl, substituted (C$_1$-C$_6$) alkyl, (C$_1$-C$_6$) alkenyl, substituted (C$_1$-C$_6$) alkenyl, (C$_1$-C$_6$) alkynyl, substituted (C$_1$-C$_6$) alkynyl, (C$_5$-C$_{20}$) aryl, substituted (C$_5$-C$_{20}$) aryl, (C$_6$-C$_{26}$) alkaryl, substituted (C$_6$-C$_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The amino acid residue Cys (C) is unusual in that it can form disulfide bridges with other Cys (C) residues or other sulfanyl-containing amino acids. The ability of Cys (C) residues (and other amino acids with —SH containing side chains) to exist in a peptide in either the reduced free —SH or oxidized disulfide-bridged form affects whether Cys (C) residues contribute net hydrophobic or hydrophilic character to a peptide. While Cys (C) exhibits a hydrophobicity of 0.29 according to the normalized consensus scale of Eisenberg (Eisenberg, 1984, supra), it is to be understood that for purposes of the present invention Cys (C) is categorized as a polar hydrophilic amino acid, notwithstanding the general classifications defined above.

As will be appreciated by those of skill in the art, the above-defined categories are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, especially in light of the detailed disclosure provided herein. In certain embodiments the substituted or altered form of the Apo A-I Milano is not Apo A-I.

The Apo A-I Milano utilized in the invention can be obtained from any source available. For example, the Apo A-I Milano can be recombinant, synthetic, semi-synthetic or purified Apo A-I Milano. In a preferred embodiment, the Apo A-I Milano can be a recombinant protein (rApo A-I Milano) expressed in yeast or *E. coli* as described in U.S. Pat. No. 5,721,114 and European Patents EP 0 469 017 and EP 0 267 703, incorporated herein by reference in their entireties. Methods for obtaining Apo A-I Milano, utilized by the invention are well-known in the art. For example, Apo A-I Milano can be separated from plasma, for example, by density gradient centrifugation followed by delipidation of the lipoprotein, reduction, denaturezation and gel-filtration chromatography, ion-exchanging chromatography, hydrophobic, e.g., phenyl sepharose, interaction chromatography or immunoaffinity chromatography, or produced synthetically, semi-synthetically or using recombinant DNA techniques known to those skilled in the art and subsequent purification familiar to those skilled in the art. (See, e.g., U.S. Pat. Nos. 6,107,467; 6,559,284; 6,423,830; 6,090,921; 5,834,596; 5,990,081; 6,506,879, Mulugeta et al., 1998, *J. Chromatogr.* 798(1-2): 83-90; Chung et al., 1980, *J. Lipid Res.* 21(3):284-91; Cheung et al., 1987, *J. Lipid Res.* 28(8):913-29; Persson, et al., 1998, *J. Chromatogr.* 711:97-109; U.S. Pat. Nos. 5,059,528, 5,834, 596, 5,876,968 and 5,721,114; and PCT Publications WO 86/04920 and WO 87/02062).

If the Apo A-I Milano is obtained from natural sources, it can be obtained from any animal source of any species. In certain embodiments, the Apo A-I Milano can be obtained from a mammalian source. In certain embodiments, the Apo A-I Milano can be obtained from a human source. In preferred embodiments of the invention, the Apo A-I Milano is derived from the same species as the subject to which the Apo A-I Milano is administered. In a preferred embodiment, the Apo A-I Milano is a recombinant Apo A-I Milano protein (rApo A-I Milano).

5.4. Methods of Administration

The Apo A-I Milano:phospholipid complexes or pharmaceutical formulations thereof can be administered by any suitable route known to those of skill in the art that ensures bioavailability in the circulation. Any route of administration that provides a therapeutically effective amount of the formulations of the invention can be used. The route of administration can be indicated by the type of pharmaceutical formulation. For example, injectable formulations can be administered parenterally, including, but not limited to, intravenous (IV), intramuscular (IM), intradermal, subcutaneous (SC), intracoronary, intraarterially, pericardially, intraarticular and intraperitoneal (IP) injections. (See, e.g., Robinson et al., 1989, In: Pharmacotherapy: A Pathophysiologic Approach, Ch. 2, pp. 15-34, incorporated herein by reference in its entirety.)

In a preferred embodiment, the Apo A-I Milano:phospholipid complexes or pharmaceutical formulations thereof can be administered parenterally. In a more preferred embodiment, the parenteral administration is intravenous. An intravenous administration can be as a bolus, for example, administered over about 2-3 minutes or by continuous infusion, for example, by means of a pump over about 1 hour or continuously infused, over about 24 hours. In a preferred embodiment, the infusion can be over about 1 to about 3 hours.

The methods provide for intravenous infusion of the pharmaceutical formulations described herein. Any suitable vessel can be used as the infusion site, including peripheral vessels such as at the antecubital fossa of the arm or a central line into the chest. In preferred embodiments, the pharmaceutical formulation is infused into the cephalic or median cubital vessel at the antecubital fossa in the arm of a subject.

In certain embodiments, administration can be by a mechanical pump or delivery device, e.g., a pericardial delivery device (PerDUCER®) or cardiopulmonary bypass machine.

5.5 Lipid Complexes

In certain embodiments, the methods of the invention comprise administration of lipid complexes of Apo A-I Milano. In certain embodiments, the invention provides pharmaceutical formulations of Apo A-I Milano:phospholipid complexes. Efficacy can be enhanced by the complexing of lipids to Apo A-I Milano. Typically, the lipid is mixed with the Apo A-I Milano prior to administration. Apo A-I Milano and lipids can be mixed in an aqueous solution in appropriate ratios and can be complexed by methods known in the art including freeze-drying, detergent solubilization followed by dialysis, microfluidization, sonication, and homogenization. Complex efficiency can be optimized, for example, by varying pressure, ultrasonic frequency, or detergent concentration. An example of a detergent commonly used to prepare Apo A-I Milano:phospholipid complexes is sodium cholate.

In some cases it is preferable to administer the Apo A-I Milano alone, essentially lipid-free, to treat or prevent acute coronary syndromes. In preferred embodiments, the Apo A-I Milano:lipid complex is administered to a subject in need thereof.

In one embodiment, the Apo A-I Milano:phospholipid complex can be in solution with an appropriate pharmaceutical diluent. In another embodiment, freeze-dried or lyophilized preparations of Apo A-I Milano:phospholipid complexes can be hydrated or reconstituted with an appropriate pharmaceutical diluent prior to administration. In another embodiment, the Apo A-I Milano:lipid complexes can be frozen preparations that are thawed until a homogeneous solution is achieved prior to administration to a subject in need thereof.

The lipid can be any suitable lipid known to those of skill in the art. Non-phosphorus containing lipids can be used, including stearylamine, dodecylamine, acetyl palmitate, (1,3)-D-mannosyl-(1,3)diglyceride, aminophenylglycoside, 3-cholesteryl-6'-(glycosylthio)hexyl ether glycolipids, N-(2, 3-di(9-(Z)-octadecenyloxy))-prop-1-yl-N,N,N-trimethylammonium chloride and fatty acid amides. In preferred embodiments, the lipid is a phospholipid.

The phospholipid can be obtained from any source known to those of skill in the art. For example, the phospholipid can be obtained from commercial sources, natural sources or by synthetic or semi-synthetic means known to those of skill in the art (Mel'nichuk et al., 1987, Ukr. Biokhim. Zh. 59(6):75-7; Mel'nichuk et al., 1987, Ukr. Biokhim. Zh. 59(5):66-70; Ramesh et al., 1979, J. Am. Oil Chem. Soc. 56(5):585-7; Patel and Sparrow, 1978, J. Chromatogr. 150(2):542-7; Kaduce et al., 1983, J. Lipid Res. 24(10):1398-403; Schlueter et al., 2003, Org. Lett. 5(3):255-7; Tsuji et al., 2002, Nippon Yakurigaku Zasshi 120(1):67P-69P).

In preferred embodiments, the lipid can be a phospholipid. The phospholipid can be any phospholipid known to those of skill in the art. For example, the phospholipid can be a small alkyl chain phospholipid, phosphatidylcholine, egg phosphatidylcholine, soybean phosphatidylcholine, dipalmitoylphosphatidylcholine, soy phosphatidylglycerol, egg phosphatidylglycerol, distearoylphosphatidylglycerol, dimyristoylphosphatidylcholine, distearoylphosphatidylcholine, dilaurylphosphatidylcholine, 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine, 1-palmitoyl-2-oleoylphosphatidylcholine, 1-oleoyl-2-palmitylphosphatidylcholine, dioleoylphosphatidylethanolamine, dilauroylphosphatidylglycerol, phosphatidylserine, phosphatidylethanolamine, phosphatidylinositol, phosphatidylglycerol, diphosphatidylglycerol, dimyristoylphosphatidylglycerol, dipalmitoylphosphatidylglycerol, distearoylphosphatidylglycerol, dioleoylphosphatidylglycerol, phosphatidic acid, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, sphingomyelin, sphingolipids, brain sphingomyelin, dipalmitoylsphingomyelin, distearoylsphingomyelin, galactocerebroside, gangliosides, cerebrosides, phosphatidylglycerol, phosphatidic acid, lysolecithin, lysophosphatidylethanolamine, cephalin, cardiolipin, dicetylphosphate, distearoyl-phosphatidylethanolamine and cholesterol and its derivatives.

The phospholipid can also be a derivative or analogue of any of the above phospholipids. In certain embodiments, the Apo A-I Milano:phospholipid complex can comprise combinations of two or more phospholipids.

In preferred embodiments, the methods of the invention provide for administration of Apo A-I Milano:phospholipid complex. In a more preferred embodiment, the lipid is a phospholipid, preferably, 1-palmitoyl-2-oleoyl phosphatidylcholine ("POPC") or ("1-palmitoyl-2-oleoyl-sn-glycero-3-phosphocholine"). In yet a more preferred embodiment, the Apo A-I Milano:POPC complex comprises about a one to one ratio by weight of Apo A-I Milano:POPC. In a most preferred embodiment, the Apo A-I Milano: POPC complex is a pharmaceutical formulation. The Apo A-I Milano:POPC complex is referred to as ETC-216.

The complex comprising Apo A-I Milano and a lipid can comprise any amount of lipid, preferably phospholipid, and any amount of Apo A-I Milano effective to treat or prevent acute coronary syndromes. In certain embodiments, the Apo A-I Milano can comprise a complex of Apo A-I Milano and a phospholipid in a ratio of about one to about one by weight. However, the Apo A-I Milano can comprise complexes with other ratios of phospholipid to Apo A-I Milano such as about 100:1, about 10:1, about 5:1, about 3:1, about 2:1, about 1:1, about 1:2, about 1:3, about 1:5, about 1:10 and about 1:100 (wt of protein/wt of lipid). A ratio by weight of between about 1:0.5 to about 1:3 (wt of protein/wt of lipid), more preferably a ratio of about 1:0.8 to about 1:1.2 (wt of protein/wt of lipid) is preferred to produce the most homogenous population and for purposes of producing stable and reproducible batches. In an even more preferred embodiment, the ratio of Apo A-I Milano to phospholipid is 1:0.95 (wt of protein/wt of lipid).

Additional lipids suitable for use in the methods of the invention are well known to persons of skill in the art and are cited in a variety of well known sources, e.g., McCutcheon's Detergents and Emulsifiers and McCutcheon's Functional Materials, Allured Publishing Co., Ridgewood, N.J., both of which are incorporated herein by reference. Generally, it is desirable that the lipids are liquid-crystalline at 37° C., 35° C., or 32° C. Lipids in the liquid-crystalline state typically accept cholesterol more efficiently than lipids in the gel state. As subjects typically have a core temperature of about 37° C., lipids that are liquid-crystalline at 37° C. are generally in a liquid-crystalline state during treatment.

5.6. Preparation of Lipid Complexes

The Apo A-I Milano:lipid complexes can be made by any method known to one of skill in the art. In some cases it is desirable to mix the lipid and Apo A-I Milano prior to administration. Lipids can be in solution or in the form of liposomes or emulsions formed using standard techniques such as homogenization, sonication or extrusion. Sonication is generally performed with a tip sonifier, such as a Branson tip sonifier, in an ice bath. Typically, the suspension is subjected to several sonication cycles. Extrusion can be carried out by biomembrane extruders, such as the Lipex Biomembrane Extruder™ (Lipex Biomembrane Extruder, Inc. Vancouver, Canada). Defined pore size in the extrusion filters can generate unilamellar liposomal vesicles of specific sizes. The liposomes can also be formed by extrusion through an asymmetric ceramic filter, such as a Ceraflow Microfilter™, commercially available from the Norton Company, Worcester Mass. or through a polycarbonate filter or other types of polymerized materials (i.e. plastics) known to those of skill in the art.

An Apo A-I Milano:lipid complex can be prepared in a variety of forms, including, but not limited to vesicles, liposomes or proteoliposomes. A variety of methods well known to those skilled in the art can be used to prepare the Apo A-I Milano:lipid complexes. A number of available techniques for preparing liposomes or proteoliposomes can be used. For example, Apo A-I Milano can be co-sonicated (using a bath or probe sonicator) with the appropriate lipid to form lipid complexes. In certain embodiments, Apo A-I Milano can be combined with preformed lipid vesicles resulting in the spontaneous formation of an apolipoprotein:lipid complex. In another embodiment, the Apo A-I Milano can also be made by a detergent dialysis method; e.g., a mixture of Apo A-I Milano, lipid and a detergent such as cholate can be dialyzed to remove the detergent and reconstituted to make the lipid complexes. (See, e.g., Jonas et al., 1986, *Methods Enzymol.* 128, 553-82).

In another embodiment, the lipid complexes can be made by co-lyophilization, as described in U.S. Pat. Nos. 6,287,590 and 6,455,088, the contents of which are hereby incorporated by reference in their entirety. Other methods are disclosed, for example, in U.S. Pat. Nos. 6,004,925, 6,037,323 and 6,046,166, incorporated herein by reference in their entireties. Other methods of preparing Apo A-I Milano:lipid complexes will be apparent to those of skill in the art.

In a preferred embodiment, the lipid complexes can be made by homogenization. In preferred embodiments, the making of Apo A-I Milano:lipid complexes begins when recombinant Apo A-I Milano is diluted to a concentration of 15 mg/ml in solution with water for injection. Sodium phosphate is added to a final concentration of 9-15 mM phosphate and to adjust the pH to between about 7.0 and about 7.8. Mannitol is added to achieve a concentration of about 0.8% to about 1% mannitol (w/v). Then POPC is added to achieve a mixture of about 1:0.95 (wt protein/wt lipid) of Apo A-I Milano dimer to POPC. The mixture is stirred at 5000 rpm for about 20 minutes using an overhead propeller and an Ultra Turrax while maintaining the temperature between 37° C. to 43° C. The feed vessel is stirred continuously at 300 rpm while the temperature is maintained between 32° C. to 43° C. with in-line heat exchangers (Avestin, Inc.). Homogenization for the first 30 minutes is carried out at 50 MPa (7250 psi) and thereafter, the pressure is maintained at 80-120 MPa (11600-17400 psi) until in-process testing by gel permeation chromatography demonstrates the % AUC of >70% between protein standards. The complexes may also be made as 10 mg/ml, 11 mg/ml, 12 mg/ml, 13 mg/ml and 14 mg/ml formulations wherein the weight is that of protein.

5.7. Combination Therapy

The Apo A-I Milano or lipid complexes or pharmaceutical formulations thereof can be used alone or in combination therapy with other interventions in the methods of the present invention. Such therapies include, but are not limited to simultaneous or sequential administration of other drugs.

In certain embodiments, the methods and formulations of the invention can be used in combination with other drugs to achieve the methods provided herein. The co-administration of another drug can be to treat, prevent or ameliorate accompanying diseases, conditions, disorders or symptoms, for example, antiarrhythmic drugs administered treat a co-existing arrhythmia. In certain embodiments, the methods provide for co-administration of drugs to treat or prevent pain accompanying acute coronary syndromes.

As described above, conventional therapy for ischemic events, including myocardial infarction, angina and acute coronary syndromes have not targeted the underlying pathology of ruptured or unstable atherosclerotic plaques. For example, a subject presenting with cardiac chest discomfort or other ischemic symptoms can be prepared for emergent percutaneous coronary intervention (PCI) with anti-clotting or antithrombotic drugs such as aspirin, clopidogrel, heparin, eptifibatide or abciximab. Beta-adrenergic blockers (β-blockers) can be administered to decrease heart rate. The administration of angiotensin converting enzyme inhibitors (ACE inhibitors) is recommended for subjects suffering from concomitant congestive heart failure (CHF) or left ventricular (LV) dysfunction. For subjects that have been resuscitated from sudden cardiac death, the administration of amiodarone is recommended. Oxygen is often supplied to the subject, generally by mask or nasal cannula and vital signs closely monitored, including, oxygen saturation via pulse oximetry. For long term treatment, statins of HMGCoA reductase inhibitor are often administered to the subject to reduce LDC levels.

For example, the Apo A-I Milano or lipid complex or pharmaceutical formulation thereof can be administered with other pharmaceutically active drugs including, but not limited to, alpha/beta adrenergic antagonists, antiadrenergic agents, alpha-1 adrenergic antagonists, beta adrenergic antagonists, AMP kinase activators, angiotensin converting enzyme (ACE) inhibitors, angiotensin II receptor antagonists, calcium channel blockers, antiarrhythmic agents, vasodilators, nitrates, vasopressors, inotropic agents, diuretics, anticoagulation agents, antiplatelet aggregation agents, thrombolytic agents, antidiabetic agents, antioxidants, anti-inflammatory agents, bile acid sequestrants, statins, cholesterol ester transfer protein (CETP) inhibitors, cholesterol reducing agents/lipid regulators, drugs that block arachidonic acid conversion, estrogen replacement therapy, fatty acid analogues, fatty acid synthesis inhibitors, fibrates, histidine, nicotinic acid derivatives, peroxisome proliferator activator receptor agonists or antagonists, fatty acid oxidation inhibitors, thalidomide or thiazolidinediones (*Drug Facts and Comparisons*, updated monthly, January 2003, Wolters Kluwer Company, St. Louis, Mo.; *Physicians Desk Reference* (56$^{th}$ edition, 2002) Medical Economics).

Other drugs singly or in combination, that can add to or can synergize the beneficial properties of the Apo A-I Milano, lipid complexes or pharmaceutical formulations thereof include but are not limited to: Alpha/Beta Adrenergic Antagonists ("β-blockers") such as, carvediol, (Coreg®); labetalol HCl, (Normodyne®); Antiadrenergic Agents such as guanadrel, (Hylorel®); guanethidine, (Ismelin®); reserpine, clonidine, (Catapres® and Catapres-TTS®); guanfacine, (Tenex®); guanabenz, (Wytensin®); methyldopa and methyldopate, (Aldomet®); Alpha-1 Adrenergic Antagonist such as doxazosin, (Cardura®); prazosin, (Minipress®); terazosin, (Hytrin®); and phentolamine, (Regitine®); Beta Adrenergic Antagonists such as sotalol, (Betapace AF® and Betapace®); timolol, (Blocadren®); propranolol, (InderalLA® and Inderal®); betaxolol, (Kerlone®); acebutolol, (Sectral®); atenolol, (Tenormin®); metoprolol, (Lopressor® and Toprol-XL®); bisoprolol, (Zebata®); carteolol, (Cartrol®); esmolol, (Brevibloc®); naldolol, (Corgard®); penbutolol, (Levatol®); and pindolol, (Visken®); AMP kinase activators such as ESP 31015, (ETC-1001); ESP 31084, ESP 31085, ESP 15228, ESP 55016 and ESP 24232; gemcabene (PD 72953 and CI-1027); and MEDICA 16; Angiotensin Converting Enzyme (ACE) Inhibitors such as quinapril, (Accupril®); benazepril, (Lotensin®); captopril, (Capoten®)); enalapril, (Vasotec®); ramipril, (Altace®); fosinopril (Monopril®); moexipril, (Univasc®); lisinopril, (Prinivil® and Zestril®); trandolapril, (Mavik®), perindopril, (Aceon®); and Angiotension II Receptor Antagonists such as candesaartan, (Atacand®); irbesartan, (Avapro®); losartan, (Cozaar®); valsartan, (Diovan®); telmisartan, (Micardis®); eprosartan, (Tevetan®); and olmesartan, (Benicar®); Calcium Channel Blockers such as nifedipine, (Adalat®, Adalat CC®, Procardia® and Procardia XL®); verapamil, (Calan®, CalanSR®, Covera-HS®, IsoptinSR®, Verelan® and VerelanPM®); diltiazem, (Cardizem®, CardizemCD® and Tiazac®); nimodipine, (Nimotop®); amlodipine, (Norvasc®); felodipine, (Plendil®); nisoldipine, (Sular®); bepridil, (Vascor®); isradipine, (DynaCirc®); and nicardipine, (Cardene®); Antiarrhythmics such as various quinidines; procainamide, (Pronestyl® and Procan®); lidocaine, (Xylocaine®); mexilitine, (Mexitil®); tocainide, (Tonocard®); flecainide, (Tambocor®); propafenone (Rythmol®), moricizine, (Ethmozine®); ibutilide, (Covert®); disopyramide, (Norpace®); bretylium, (Bretylol®); amiodarone, (Cordarone®); adenosine, (Adenocard®); dofetilide (Tikosyn®); and digoxin, (Lanoxin®); Vasodilators such as diazoxide, (Hyperstat IV®); hydralazine, (Apresoline®); fenoldopam, (Corolpam®); minoxidil, (Loniten®); and nitroprusside, (Nipride®); Nitrates such as isosorbide dinitrate; (Isordil® and Sorbitrate®); isosorbide mononitrate, (Imdur®, Ismo® and Monoket®); Nitroglycerin paste, (Nitrol®); various nitroglycerin patches; nitroglycerin SL, (Nitrostat®), Nitrolingual spray; and nitroglycerin IV, (Tridil®); Vassopressors such as norepinephrine, (Levophed®); and phenylephrine, (Neo-Synephrine®); Inotrophic Agents such as amrinone; (Inocor®); dopamine, (Intropine®); dobutamine, (Dobutrex®); epinephrine, (Adrenalin®); isoproternol, (Isuprel®), milrinone, (Primacor®); Diuretics such as spironolactone, (Aldactone®); torsemide, (Demadex®); hydroflumethiazide, (Diucardin®); chlorothiazide, (Diuril®); ethacrynic acid, (Edecrin®); hydrochlorothiazide, (hydroDIURIL® and Microzide®); amiloride, (Midamor®); chlorthalidone, (Thalitone® and Hygroton®); bumetanide, (Bumex®); furosemide, (Lasix®); indapamide, (Lozol®); metolazone, (Zaroxolyn®); triamterene, (Dyrenium®); and combinations of triamterene and hydrochlorothiazide (Dyazide® and Maxzide®); Antithrombotics/Anticoagulants/Antiplatelet such as bivalirudin, (Angiomax®); lepirudin, (Refludan®); various heparins; danaparoid, (Orgaran®); various low molecular weight heparins; dalteparin (Fragmin®); enoxaparin (Lovenox®); tinzaparin, (Innohep®); warfarin, (Coumadin®); dicumarol, (Dicoumarol®); anisindione, (Miradone®); aspirin; argatroban, (Argatroban®); abciximab, Reopro®); eptifibatide, (Integrilin®); tirofiban, (Aggrastat®); clopidogrel, (Plavix®); ticlopidine, (Ticlid®); and dipyridamole, (Persantine®); Thrombolytics such as alteplase, (Activase®); tissue plasminogen activator (TPA), (Activase®); anistreplase, APSAC, (Eminase®); reteplase, rPA, (Retavasae®); steptokinase, SK, (Streptase®); urokinase, (Abbokinase®); Antidiabetic agents such as metformin, (Glucophage®); glipizide, (Glucotrol®); chlorpropamide, (Diabinese®); acetohexamide, (Dymelor®); tolazamide, (Tolinase®); glimepride, (Amaryl®); glyburide, (DiaBeta® and Micronase®); acarbose, (Precose®); miglitol, (Glyset®); repaflinide, (Prandin®); nateglinide, (Starlix®); rosiglitazone, (Avandia®); and pioglitazone (Actos®); Antioxidants and anti-inflammatory agents; Bile Acid Sequestrants such as cholestyramine, (LoCholest®, Prevalite® and Questran®); colestipol, (Colestid®); and colesevelam, (Welchol®); Statins (drugs that inhibit HMGCoA reductase) such as rovastatin, (Crestor®); fluvastatin, (Lescol®); atorvastatin, (Lipitor®); lovastatin, (Mevacor®); pravastatin, (Pravachol®); and simvastatin, (Zocor®); CETP inhibitors; drugs that block arachidonic acid conversion: Estrogen replacement therapy; Fatty acid analogues such as PD 72953, MEDICA 16, ESP 24232, and ESP 31015; Fatty acid synthesis inhibitors; fatty acid synthesis inhibitors; fatty acid oxidation inhibitors, ranolazine, (Ranexa®); Fibrates such as clofibrate, (Atromid-S®); gemfibrozil, (Lopid®); micronized fenofibrate capsules, (Tricor®); bezafibrate and ciprofibrate; histidine; Nicotinic Acid derivatives such as niacin extended-release tablets, (Niaspan®); Peroxisome proliferator activator receptor agonists and antagonists; thalidomide, (Thalomid®) and compounds described in U.S. Pat. Nos. 6,459,003, 6,506,799 and U.S. Application Publication Nos. 20030022865, 20030018013, 20020077316, and 20030078239 the contents of which are incorporated herein by reference in their entireties.

Other drugs singly or in combination, that can add to or can synergize the beneficial properties of the Apo A-I Milano or lipid complexes or pharmaceutical formulations thereof include, for example, anti-proliferative drugs like paclitaxel and topotecan, (Brehm et al. 2001, *Biochemical Pharmacology*, 61(1):119-127) and anti-inflammatory drugs such as steroidal and non-steroidal anti-inflammatory agents (including cyclooxygenase-2 (COX-2) inhibitors).

5.8. Pharmaceutical Formulations

In one aspect, the present invention provides formulations for the treatment, reduction or prevention of injury from acute coronary syndromes by administering a pharmaceutical formulation comprising Apo A-I Milano. In preferred embodiments the Apo A-I Milano(Apo A-I Milano) can be complexed with a lipid. In a more preferred embodiment, the Apo A-I Milano is complexed with POPC.

The Apo A-I Milano or lipid complexes thereof can be administered in the form of a pharmaceutical formulation. A pharmaceutical formulation, as described herein, includes the addition of, for example, an acceptable diluent, excipient, vehicle or carrier. As is known in the art, the addition of one or more diluents, excipients, vehicle or carriers renders a formulation suitable for administration to a subject and can bestow other favorable properties such as extended shelf life.

The pharmaceutical formulations typically comprise a pharmaceutically acceptable carrier or vehicle. Many pharmaceutically acceptable carriers or vehicles can be employed. The example described herein utilizes sucrose-mannitol. Normal saline is often employed as the pharmaceutical carrier or vehicle. Other suitable carriers or vehicles include glucose, trehalose, sucrose, sterile water, buffered water, 0.45% saline (half Normal saline), and 0.3% glycine, and can further include glycoproteins for enhanced stability, such as albumin. These formulations can be sterilized by conventional, well known sterilization techniques. The resulting aqueous solutions can be packaged for use or filtered under aseptic conditions and lyophilized (freeze-dried). The lyophilized preparation can then be combined with a sterile aqueous solution prior to administration.

The pharmaceutical formulations can also contain pharmaceutically acceptable excipients as required to approximate physiological conditions, such as pH adjusting and buffering agents, and tonicity adjusting agents, for example, sodium acetate, sodium lactate, sodium chloride, potassium chloride, and calcium chloride. Antibacterial agents, for example, phenol, benzalkonium chloride or benzethonium chloride, can be added to maintain sterility of a product, especially pharmaceutical formulations intended for multi-dose parenteral use. Suspending, stabilizing and/or dispersing agents can also be used in the formulations of the invention.

The pharmaceutical formulations can comprise the apolipoprotein (Apo A-I Milano) in a salt form. For example, because proteins can comprise acidic and/or basic termini and/or side chains, the Apo A-I Milano can be in the pharmaceutical formulations as either free acids or bases, or as pharmaceutically acceptable salts. Pharmaceutically acceptable salts can include, suitable acids capable of forming salts with Apo A-I Milano including, for example, inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming salts with Apo A-I Milano can include, for example, inorganic bases such as sodium hydroxide, ammonium hydroxide, potassium hydroxide and the like; and organic bases such as mono-, di- and tri-alkyl amines (e.g., triethyl amine, diisopropyl amine, methyl amine, dimethyl amine and the like) and optionally substituted ethanolamines (e.g., ethanolamine, diethanolamine and the like).

The pharmaceutical formulation can be in a variety of forms suitable for any route of administration, including, but not limited to, parenteral, enteral, topical or inhalation. Parenteral administration refers to any route of administration that is not through the alimentary canal, including, but not limited to, injectable administration (i.e., intravenous, intramuscular and the like as described herein). Enteral administration refers to any route of administration using the alimentary canal, oral or rectal including, but not limited to, tablets, capsules, oral solutions, suspensions, sprays and the like, as described herein. For purposes of this application, enteral administration also refers to vaginal routes of administration. Topical administration refers to any route of administration through the skin, including, but not limited to, creams, ointments, gels and transdermal patches, as described herein (see also, Remington's Pharmaceutical Sciences, 18$^{th}$ Edition Gennaro et al., eds.) Mack Printing Company, Easton, Pa., 1990).

Parenteral pharmaceutical formulations of the present invention can be administered by injection, for example, into a vein (intravenously), an artery (intraarterially), a muscle (intramuscularly), under the skin (subcutaneously or in a depot formulation), to the pericardium, to the coronary arteries. The injectable pharmaceutical formulations can be a pharmaceutically appropriate formulation for administration directly into the heart, pericardium or coronary arteries. In preferred embodiments, the pharmaceutical formulations are infused into a peripheral vessel of a subject, e.g. at the arm or antecubital fossa.

Injectable pharmaceutical formulations can be sterile suspensions, solutions or emulsions in aqueous or oily vehicles. The formulations for injection can be presented in unit dosage form, e.g., in ampules or in multidose containers, and can comprise added preservatives. Preferred buffers for parenteral pharmaceutical formulations are phosphate, citrate and acetate.

In another embodiment, the pharmaceutical formulation can be provided in powder form for reconstitution with a suitable vehicle, including but not limited to sterile pyrogen free water; saline or dextrose before use. To this end, the Apo A-I Milano can be lyophilized, or co-lyophilized with a lipid, as described above, as appropriate. In another embodiment, the pharmaceutical formulations can be supplied in unit dosage forms and reconstituted prior to use.

For prolonged delivery, the pharmaceutical formulation can be provided as a depot preparation, for administration by implantation; e.g., subcutaneous, intradermal, or intramuscular injection. Thus, for example, the pharmaceutical formulation can be formulated with suitable polymeric or hydrophobic materials (e.g., as an emulsion in an acceptable oil) or ion exchange resins, or as sparingly soluble derivatives; e.g., as a sparingly soluble salt form of the Apo A-I Milano or Apo A-I Milano:lipid complex.

In another embodiment, the pharmaceutical formulation is a transdermal delivery system manufactured as an adhesive disc or patch that slowly releases the active ingredient for percutaneous absorption. In this embodiment, permeation enhancers can be used to facilitate transdermal penetration of the Apo A-I Milano. In another embodiment, the transdermal pharmaceutical formulation can further contain nitroglycerin for use in patients with angina.

For administration by inhalation, the pharmaceutical formulation can be delivered by aerosol spray from pressurized packs or via nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount, for example, a metered dose inhaler. Capsules and cartridges of e.g., gelatin for use in an inhaler or insufflator can be formulated comprising a powder mix of the Apo A-I Milano and a suitable powder base such as lactose or starch.

The formulations can, if desired, be presented in a pack or dispenser device that can comprise one or more unit dosage forms comprising the Apo A-I Milano pharmaceutical formulations. The pack can for example, comprise metal or plastic foil, such as a blister pack. The pack or dispenser device can be accompanied by instructions or labeling for administration.

In certain embodiments, the pharmaceutical formulation of the ApoAI-M or Apo A-I Milano:lipid complex can comprise a concentration of Apo A-I Milano sufficient to treat a subject in need thereof. In certain embodiments, the pharmaceutical formulation of the Apo A-I Milano or Apo A-I Milano:lipid complex can comprise a concentration of Apo A-I Milano of about 5 mg/ml to about 50 mg/ml. In preferred embodiments, the formulations can comprise Apo A-I Milano in a concentration of about 10 mg/ml to about 20 mg/ml. In a more preferred embodiment, the formulations can comprise Apo A-I Milano in a concentration of about 13 mg/ml to about 16 mg/ml. The concentration of Apo A-I Milano can be determined by any suitable technique known to those of skill in the art. In certain embodiments, the concentration of Apo A-I Milano is determined by size exclusion high performance liquid chromatography (SE-HPLC).

In certain embodiments, the pharmaceutical formulation of the ApoAI-M or Apo A-I Milano:lipid complex can comprise a concentration of lipid sufficient to form complexes with Apo A-I Milano. In certain embodiments, the lipid is a phospholipid. In preferred embodiments, the lipid is POPC. In certain embodiments, pharmaceutical formulation of the Apo A-I Milano or Apo A-I Milano:lipid complex can comprise a concentration of POPC of about 1 mg/ml to about 50 mg/ml. In preferred embodiments, formulations can comprise POPC in a concentration of about 5 mg/ml to about 25 mg/ml. In a more preferred embodiment, the formulations can comprise POPC in a concentration of about 10 mg/ml to about 20 mg/ml. In an even more preferred embodiment, the formulations can comprise POPC in a concentration of about 11 mg/ml to about 17 mg/ml. The concentration of POPC can be determined by any suitable technique known to those of skill in the art. In certain embodiments, the concentration of POPC is determined by high performance liquid chromatography.

In preferred embodiments, the pharmaceutical formulation of the Apo A-I Milano:lipid complex can comprise sucrose in an amount sufficient to make a pharmaceutically suitable formulation of Apo A-I Milano or Apo A-I Milano:lipid complex. In certain embodiments, the pharmaceutical formulations can comprise about 0.5% to about 20% sucrose. In certain embodiments, the pharmaceutical formulations can comprise about 3% to about 12% sucrose. In certain embodiments, the pharmaceutical formulations can comprise about 5% to about 7% sucrose. In preferred embodiments, the pharmaceutical formulations can comprise about 6.0% to about 6.4% sucrose. In a most preferred embodiment, the pharmaceutical formulation can comprise 6.2% sucrose.

In preferred embodiments, the pharmaceutical formulation of the Apo A-I Milano:lipid complex can comprise mannitol in an amount sufficient to make a pharmaceutically suitable formulation of Apo A-I Milano or Apo A-I Milano:lipid complex. In certain embodiments, the pharmaceutical formulations can comprise about 0.01% to about 5% mannitol. In certain embodiments, the pharmaceutical formulations can comprise about 0.1% to about 3% mannitol. In certain embodiments, the pharmaceutical formulations can comprise about 0.5% to about 2% sucrose. In preferred embodiments, the pharmaceutical formulations can comprise about 0.8% to about 1% mannitol. In a most preferred embodiment, the pharmaceutical formulation can comprise 0.9% mannitol.

In certain embodiments, the pharmaceutical formulation of the Apo A-I Milano:lipid complex can comprise a buffer in an amount sufficient to make a pharmaceutically suitable formulation of Apo A-I Milano or Apo A-I Milano:lipid complex. In certain embodiments, the pharmaceutical formulations can comprise a phosphate buffer. In certain embodiments, the buffer concentration can be about 3 mM to about 25 mM. In certain embodiments, the buffer concentration can be about 5 mM to about 20 mM. In preferred embodiments, the buffer concentration can be about 8 mM to about 15 mM. In certain embodiments, an appropriate buffer is added to adjust the pH of the pharmaceutical formulation to a range suitable for administration to a subject. In certain embodiments, the pharmaceutical formulation can have a pH of about 6.8 to about 7.8. In certain embodiments, the pharmaceutical formulation can have a pH of about 7.0 to about 7.8. In certain embodiments, the pharmaceutical formulations can have a pH of about 7.2 to about 7.5. In preferred embodiments, the pharmaceutical formulation can have a pH of about 7.5.

In certain embodiments, the pharmaceutical formulation of the Apo A-I Milano:lipid complex has an osmolality that is suitable for administration to a subject. In certain embodiments, the osmolality of the formulation can be about 200 to about 400 mOsm. In certain embodiments, the pharmaceutical formulation can have an osmolality of about 220 to about 380 mOsm. In certain embodiments, the pharmaceutical formulation can have an osmolality of about 260 mOsm to about 340 mOsm. In preferred embodiments, the pharmaceutical formulation can have an osmolality of about 280 mOsm to about 320 mOsm. In a most preferred embodiment, the pharmaceutical formulation can have an osmolality of about 290 mOsm.

The formulations of the invention provide an Apo A-I Milano:lipid complex of sufficient purity to allow administration to a subject. In certain embodiments, the pharmaceutical formulation can comprise Apo A-I Milano at a purity of about 98% or more, about 96% or more, about 95% or more, about 93% or more, about 91% or more or about 90% or more. In a preferred embodiment, the purity of the Apo A-I Milano is about 90% or more. The purity of the Apo A-I Milano can be determined by any suitable technique known to those of skill in the art. In certain embodiments, the purity of the Apo A-I Milano can be determined by size exclusion HPLC.

The formulations of the invention provide an Apo A-I Milano:lipid complex of sufficient purity of POPC to allow administration to a subject. In certain embodiments, the pharmaceutical formulation can comprise POPC at a purity of about 98% or more, about 96% or more, about 95% or more, about 93% or more, about 91% or more or about 90% or more. In a preferred embodiment, the purity of the POPC is greater than about 90%. The purity of the POPC can be determined by any suitable technique known to those of skill in the art. In certain embodiments, the purity of the POPC can be determined by HPLC.

In certain preferred embodiments, the Apo A-I Milano:lipid complex has lipid hydroperoxide amounts of about 10%, or less, about 8% or less, about 6% or less, about 4% or less, about 2% or less, about 1% or below detectable limits as determined by the ferrous oxidation/xylenol orange assay (Jiang, et al. 1992, *Anal. Biochem* 202: 384-389). In certain embodiments the Apo A-IM:POPC complex has a purity of greater than 85% (measured as % of total peak area) as determined by gel permeation chromatography. In certain embodiments, the formulation has little or no endotoxins. In preferred embodiments, the formulation has endotoxins of <0.04 EU/mg Apo A-I Milano.

In certain embodiments, the formulation can amount of particulates greater than 10 μm in size is < about 6,000 per 50 mL vial as determined by light obscuration. In certain embodiments, the amount of particulates greater than 25 μm in size is <about 600 per 50 mL vial as determined by light obscuration.

In a preferred embodiment, the Apo A-I Milano:lipid complex pharmaceutical formulation is made by diluting a rApo A-I Milano to a concentration of 15 mg/ml in solution with water for injection. Sodium phosphate is added to a final concentration of 9-15 mM phosphate and to adjust the pH to between about 7.0 and about 7.8. Mannitol is added to achieve a concentration of about 0.8% to about 1% mannitol (w/v). Then POPC is added to achieve a ratio of 1:0.95 (wt protein/wt lipid) of Apo A-I Milano dimer to POPC. The mixture is stirred at 5000 rpm for about 20 minutes using an overhead propeller and an Ultra Turrax while maintaining the temperature between 37° C. to 43° C. The feed vessel is stirred continuously at 300 rpm while the temperature is maintained between 32° C. to 43° C. with in-line heat exchangers (Avestin, Inc.). Homogenization for the first 30 minutes is carried out at 50 MPa (7250 psi) and thereafter, the pressure is maintained at 80-120 MPa (11600-17400 psi) until in-process testing by gel permeation chromatography demonstrates the % AUC of greater than about 70% between protein standards. The osmolality of the complex is then adjusted to about by the addition of 6.0% to 6.4% sucrose. The pharmaceutical formulation of the Apo A-I Milano:POPC complex is then sterilized by filtration through 0.22 µM filters.

In another preferred embodiment, the pharmaceutical formulation comprises about 12 to about 18 mg/ml recombinant Apo A-I Milano, about 11 to about 17 mg/ml 1-palmitoyl-2-oleoyl-sn-glycero-3-phosphocholine at pH 7.4, with 6.2% sucrose and 0.9% mannitol with an osmolality of about 280 mOsm to about 320 mOsm. The pharmaceutical formulation can have rAPO A-I-M at about 90% purity, POPC at about 97% purity. In a certain embodiment, no single impurity can be about greater than 2%.

The pharmaceutical formulation can be stored frozen (about –15° C. to about –25° C.). In certain embodiments, the formulations can be cold solutions, frozen solutions or lyophilized solutions. It is preferred that the such formulations be thawed and warmed to room temperature prior to administration to a subject. Gentle thawing and warming is recommended to avoid denaturation of the protein.

In another preferred embodiment, the formulations can be in sterile glass vials of about 2 mL to about 250 mL, preferably about 10 mL to about 100 mL, most preferably about 50 mL containing a pharmaceutical formulation comprising an Apo A-I Milano:phospholipid complex. In certain embodiments the pharmaceutical formulations can comprise about 10 mg/mL to about 15 mg/mL of the Apo A-I Milano:phospholipid complex in a final fill volume of about 39 to 41 ml per vial. The amount of Apo A-I Milano:phospholipid complex can be about 500 mg to 750 mg per 50 mL vial.

The pharmaceutical formulations can be for a single, one-time use or can contain antimicrobial excipients, as described above, rendering the pharmaceutical formulations suitable for multiple uses, for example a multi-use vial. In certain embodiments, the pharmaceutical formulations can be in unit-of-use packages. As is known to those of skill in the art, a unit-of-use package is a convenient, prescription size, patient ready unit labeled for direct distribution by health care providers. A unit-of-use package contains a pharmaceutical formulation in an amount necessary for a typical treatment interval and duration for a given indication. The methods and formulations of the invention provide for a unit-of-use package of a pharmaceutical formulation comprising, for example, an Apo A-I Milano:phospholipid complex in an amount sufficient to treat an average sized adult male or female with 15 mg/kg once weekly for 5 weeks. In one embodiment, the unit-of-use package can comprise a pharmaceutical formulation comprising an Apo A-I Milano:phospholipid complex in an amount sufficient to treat an average sized adult subject with 45 mg/kg once weekly for 6 weeks. It will be apparent to those of skill in the art that the doses described herein are based on the subject's weight.

The pharmaceutical formulations can be labeled and have accompanying labeling to identify the formulation contained therein and other information useful to health care providers and subjects in the treatment and prevention of cardiovascular and vascular disorders, acute coronary syndromes, ischemic disorders and for the stabilization of plaques, including, but not limited to, instructions for use, dose, dosing interval, duration, indication, contraindications, warnings, precautions, handling and storage instructions and the like.

In further embodiments, the present invention provides kits for treating or preventing cardiovascular and vascular disorders, acute coronary syndromes, ischemic disorders and for the stabilization of plaques. The kits comprise one or more effective doses of Apo A-I Milano or Apo A-I Milano:lipid complex or pharmaceutical formulations thereof along with a label or labeling with instructions on using the Apo A-I Milano or Apo A-I Milano:lipid complex or pharmaceutical formulations thereof to treat or prevent acute coronary syndromes according to the methods of the invention. In certain embodiments, the kits can comprise components useful for carrying out the methods such as devices for delivering the Apo A-I Milano or Apo A-I Milano:lipid complex or pharmaceutical formulations thereof and components for the safe disposal of these devices, e.g. a sharps container. In certain embodiments, the kits can comprise Apo A-I Milano or Apo A-I Milano:lipid complex or pharmaceutical formulations thereof in a pre-filled syringes, unit-dose or unit-of-use packages.

6. EXAMPLES

The present invention will be further understood by reference to the following non-limiting examples.

6.1. Example 1

Tolerability of ETC-216

This example demonstrates the safety and tolerability of ETC-216 in healthy volunteers.

A double-blind placebo-controlled study was conducted to determine the safety and tolerability of Apo A-I Milano and phospholipid. The Apo A-I Milano was complexed with a phospholipid (POPC) in a one to one weight ratio, referred to as ETC-216. The study evaluated the safety and tolerability of five escalating doses of a single intravenous infusion of ETC-216 in healthy male volunteers and at two different doses in healthy female volunteers. Informed consent was obtained from all volunteers prior to the study.

Thirty-two healthy volunteers ("subjects") between the ages of 18-50 years of age were administered intravenous doses of ETC-216. In male subjects, doses up to and including 100 mg/kg were administered. In female subjects, doses up to and including 50 mg/kg were administered. The gender of the subject, dose and rate are provided below in Table 1.

TABLE 1

| Dose (mg protein/body weight) | Number of Subjects | Gender | Infusion Rate (mg/kg/min) |
|---|---|---|---|
| 0 (placebo) | 3 | Male | 1.67 |
| 0 (placebo) | 2 | Male | 1.25 |
| 5 | 3 | Male | 1.67 |
| 15 | 3 | Male | 1.67 |
| 50 | 3 | Male | 1.67 |
| 75 | 3 | Male | 1.25 |
| 100 | 3 | Male | 1.25 |

TABLE 1-continued

| Dose (mg protein/kg body weight) | Number of Subjects | Gender | Infusion Rate (mg/kg/min) |
|---|---|---|---|
| 0 (placebo) | 1 | Female | 1.67 |
| 0 (placebo) | 2 | Female | 0.83 |
| 15 | 3 | Female | 1.67 |
| 15 | 3 | Female | 0.83 |
| 50 | 3 | Female | 0.83 |

Adverse event monitoring included clinical laboratory evaluation, physical examination and vital signs. Subjects were monitored for 27 days following dosing.

Twenty of the 32 subjects in this study reported adverse events, all of which were mild to moderate. Adverse events that occurred in two or more subjects were considered possibly related to study drug treatment. These adverse events and number of subjects experiencing these adverse events were, lymphopenia (11 subjects), leukocytosis (10 subject), nausea (6 subjects), headache and diarrhea (4 subjects), vomiting (3 subjects) and abdominal pain and hypertriglyceridemia (2 subjects). The majority of possibly related adverse events (gastrointestinal and white cell disorders) were reported following the infusion of 50 mg/kg or 100 mg/kg of ETC-216 in male subjects. Two adverse events (hypoproteinemia and abnormal hepatic function) that occurred in placebo-treated subjects were considered possibly related to study treatment. There were no deaths, serious adverse events, or withdrawals because of adverse events.

As provided in FIG. 1, the serum levels of HDL unesterified cholesterol in male subjects 30 minutes following a single dose of ETC-216 increased at doses of 15 mg/kg and higher.

Antibody titers to Apo A-I Milano were tested in sera before infusion and up to 27 days after infusion. There was no significant antibody response in any of the subjects after single dose administration.

The terminal half-life of approximately 100 hours supports the rationale for performing the initial multiple dose study in humans with an every 7 day dosing regimen.

These results indicate that ETC-216 was safe and well tolerated at all doses and no serious adverse events occurred.

6.2. Example 2

The Efficacy of Different Doses of ETC-16 in Regressing Atherosclerosis

This example demonstrates the efficacy of 15 mg/kg and 45 mg/kg doses of ETC-216 in regressing coronary atherosclerosis in subjects with acute coronary syndromes.

This study was a randomized, double-blind, placebo controlled multiple-dose study to evaluate the efficacy and safety of ETC-216 in subjects with acute coronary syndromes as assessed by intravascular ultrasound. Prior to the initiation of any study-specific procedure, all subjects gave informed consent approved by the Institutional Review Board (IRB) of each participating institution.

Eligible subjects were those diagnosed with acute coronary syndromes (unstable angina, non Q wave myocardial infarction or ST elevation myocardial infarction) within 14 days prior to screening and who were scheduled to undergo a coronary angiography and/or percutaneous coronary intervention (PCI) and anticipating 24-hour stay following the procedure. Subjects meeting this criteria were excluded if their procedure was considered urgent and/or considered to carry a high risk of acute complications, as determined by the treating physician.

The primary efficacy endpoint was the change (end of treatment minus pretreatment) in percent atheroma volume in a 30-80 mm segment of one targeted (imaged) coronary artery assessed by intravascular ultrasound (IVUS). A positive result was defined as a negative change in percent atheroma volume with Confidence Intervals (CIs) not including zero.

Secondary efficacy endpoints were the mean change in total atheroma volume and average maximal atheroma thickness. Secondary efficacy endpoints were established for IVUS and angiography. For IVUS, the secondary efficacy endpoints were:
1) Nominal change (end of treatment minus pretreatment) in total plaque "volume" as measured by the average of plaque areas for all slices of anatomically comparable segments of the target coronary artery;
2) Nominal change (end of treatment minus pretreatment) in the average maximum plaque thickness for all slices of anatomically comparable segments of the target coronary artery;
3) Least and most diseased segment "volume":
   a) nominal change (end of treatment minus pretreatment) in segment plaque "volume" for the 10 mm contiguous slices at baseline containing the least percent plaque area (defined as the least diseased segment);
   b) nominal change (end of treatment minus pretreatment) in segment plaque "volume" for the 10 mm contiguous slices at baseline containing the greatest percent plaque area (defined as the most diseased segment).

Secondary efficacy endpoint for angiography were:
1) Mean coronary luminal diameter within all measured coronary segments;
2) Number of new angiographic lesions in each treatment subgroup;
3) Proportion of subjects with one or more new angiographic coronary lesions at the end of treatment;
4) Number of sites with a pre-existing lesion showing regression;
5) Number of sites with a pre-existing lesion showing progression;
6) Proportion of subjects showing "regression" in any pre-existing lesions;
7) Proportion of subjects showing "progression or no change" in all pre-existing lesions;
8) Proportion of subjects showing "regression or no change" in all pre-existing lesions.

The methods for IVUS were analyzed as described by Nissen 2001, Am. J. Cardiol. 87: 15A-20A, incorporated by reference herein in its entirety. Briefly, the operator digitized the IVUS videotape, reviewed the pullback and selected the origin of the most distal side-branch as the beginning point for analysis as show in FIG. 2(A). Subsequently, every $30^{th}$ image was selected for analysis, representing a series of cross-sections spaced exactly 0.5 mm apart. The final analyzed cross-section was the most proximal image in the sequence prior to the appearance of the left main coronary artery or right coronary ostium (proximal fiduciary site) as show in FIGS. 2(B)-2(D). The procedure was repeated for the follow-up examination using identical landmarks to ensure that the identical segment was analyzed at both time points.

Both directed and derived IVUS measurements were performed. Direct IVUS measurements were performed in accordance with the standards of the American College of Cardiology and European Society of Cardiology (Mintz et al. J. Am. Coll. Cardiol. 37: 1478-92, incorporated by reference herein in its entirety). Using National Institute of Health Image 1.62 (NIH public domain software), the operator performed a calibration procedure by measuring 1-mm grid marks encoded in the IVUS image by the scanner. For each cross-section, the operator performed manual planimetry to trace the leading edges of the luminal and external elastic membrane borders (FIGS. 3(A)-3(D)). The maximum atheroma thicknesses were also directly measured. The accuracy and reproducibility of these methods have been previously reported, demonstrating that, after calibration, mean IVUS cross sectional area measurements were within 0.5% of actual dimensions for precision-drilled Lucite phantoms ranging in area from 3.24 mm$^2$ to 27.99 mm$^2$ (Schoenhagen et al. 2003, *J. Am. Soc. Echocardiogr.* 16:277-84, incorporated herein by reference in its entirety). The variability of measurements by multiple observers demonstrated a standard deviation of 2.9%.

Derived IVUS measurements included calculation of atheroma area as external elastic membrane (EEM) area minus luminal area. Because image cross-sections were obtained at 0.5-mm intervals, the total atheroma volume could be calculated using the Simpson rule as mean atheroma area multiplied by pullback length in millimeters. The percent atheroma volume was computed as: ($\Sigma$ atheroma areas/$\Sigma$ EEM areas)×100 (See, e.g., Nissen et al., 2003, *JAMA* 290: 2292-2300). Analysis of coronary angiography was performed in a core laboratory at the Cleveland Clinic Foundation using standardized methods designed to reduce measurement variability. Comparison of the diameter of the angiographic catheter tip with its known dimension was used to calibrate the system The angiographic end point was the change in the mean coronary luminal diameter from baseline to follow-up.

Fifty-seven subjects were randomized to receive 15 mg/kg of ETC-216, 45 mg/kg of ETC-216 or volume matched placebo every 7$^{th}$ day (±1 day) with a maximum of up to 5 intravenous doses. The subjects were randomized to 15 mg/kg ETC-216, 45 mg/kg ETC-216 or placebo in a 2:2:1 ratio. Forty-seven subject completed the study.

The 15 mg/kg dose was infused intravenously over about 50 minutes and the 45 mg/kg dose was infused intravenously over about 150 minutes. The infusion rate was increased for some subjects due to the occurrence of nausea. All intravenous infusions were given peripherally.

Subjects were monitored by clinical laboratory parameters including antibody levels for ETC-216, physical examinations, vital signs, electrocardiograms (EKGs) and the frequency and intensity of clinical adverse events. Angiography and IVUS were conducted on each patient twice. The first time after completion of the initial screening visit and the second occurring approximately 2 weeks (±7 days) after the last dose of study drug.

Positive results were obtained with respect to the primary endpoint as summarized in Table 2, below. In the combined treatment group (patients who received either the 15 mg/kg or 45 mg/kg dose of ETC-216), the change in mean (Standard Deviation or SD) percent atheroma volume was −1.06% (3.17%). The median was −0.81% (95% CI, −1.53% to −0.34%; p=0.02 compared with baseline. For the placebo group the mean (SD) change was 0.14% (3.09%). The median was 0.03% (95% CI, −1.11% to 1.43%; p-0.97 compared with baseline).

TABLE 2

Percent Atheroma Volume in the Target Coronary Segment

| Treatment Groups | No. of subjects | Baseline Mean (SD[1]) | Baseline Median (IQR[2]) | Follow-up Mean (SD) | Follow-up Median (IQR) | Change from Baseline Mean (SD) | Change from Baseline Median (95% CI[3]) | P value[4] |
|---|---|---|---|---|---|---|---|---|
| Placebo | 11 | 34.80 (8.44) | 35.29 (26.99-39.81) | 34.94 (9.74) | 33.59 (27.07-41.09) | 0.14 (3.09) | 0.03 (−1.11 to 1.43) | 0.97 |
| ETC-216 15 mg/kg | 21 | 39.71 (7.04) | 40.55 (34.16-44.97) | 38.42 (6.5) | 38.84 (32.78-42.87) | −1.29 (3.48) | −1.14 (−2.24 to −0.56) | 0.03 |
| ETC-215 45 mg/kg | 15 | 37.92 (7.83) | 41.22 (31.92-44.10) | 37.19 (7.71) | 36.62 (32.81-44.02) | −0.73 (2.75) | −0.34 (−01.21 to 0.43) | 0.45 |
| ETC-216 Combined | 36 | 38.96 (7.32) | 40.88 (34.01-44.53) | 37.91 (6.95) | 38.17 (32.79-43.53) | −1.06 (3.17) | −0.81 (−1.53 to −0.34) | 0.02[5] |

[1]Standard Deviation.
[2]Interquartile Range.
[3]Confidence Interval.
[4]P values for within-group comparison from Wilcoxon signed rank test. For between-group comparison of ETC-216, Apo A-I Milano:POPC combined vs. placebo from analysis of covariance of ranks of change from baseline, with the baseline value as a covariate, p = 0.029.
[5]Prespecified primary efficacy end point.

With respect to the secondary endpoints, positive results were also obtained, as provided in Table 3, below. Compared with baseline, the mean (SD) change in total atheroma volume in the combined treatment group was −14.1 mm$^3$ (39.5 mm$^3$; median −13.3 mm$^3$; 95% CI, −20.7 to −7.2; p<0.001). For the placebo group, the corresponding change was −2.9 mm$^3$ (23.3 mm$^3$). The median was −0.2 mm$^3$ (23.3 mm$^3$). The median was −0.2 mm$^3$; 95% CI, −8.6 to 8.2; p=0.97). The mean (SD) change from baseline in maximum atheroma thickness for the combined treatment group was −0.042 mm (0.080 mm). The median was −0.035 mm (95% CI, −0.058 to −0.020; p<0.002). For the placebo group, the corresponding change was −0.008 mm (0.061 mm; median −0.009 (95% CI, −0.035 to 0.026; p=0.83). See Table 4, below.

TABLE 3

Total Atheroma Volume in the Target Coronary Segment

| Treatment Groups | No. of subjects | Baseline, mm$^3$ Mean (SD) | Baseline, mm$^3$ Median (IQR) | Follow-up, mm$^3$ Mean (SD) | Follow-up, mm$^3$ Median (IQR) | Change From Baseline, mm$^3$ Mean (SD) | Change From Baseline, mm$^3$ Median (95% CI) | P value[1] |
|---|---|---|---|---|---|---|---|---|
| Placebo | 11 | 172.6 (113.2) | 149.0 (58.6-216.5) | 169.8 (118.0) | 145.1 (58.4-217.8) | −2.9 (23.3) | −0.2 (−8.6 to 8.2) | 0.97 |
| ETC-216 15 mg/kg | 21 | 295.5 (166.5) | 279.7 (173.6-370.7) | 280.4 (155.6) | 265.5 (161.1-351.6) | −15.1 (50.6) | −15.0 (−29.6 to −4.9) | 0.21 |
| ETC-215 45 mg/kg | 15 | 230.6 (156.7) | 195.8 (90.9-332.9) | 218.0 (145.6) | 183.8 (89.4-311.1) | −12.6 (15.3) | −12.0 (−20.6 to −2.9) | 0.007 |
| ETC-216 Combined | 36 | 268.4 (163.5) | 263.7 (129.4-359.3) | 254.4 (152.6) | 244.8 (131.0-337.6) | −14.1 (39.5) | −13.3 (−20.7 to −7.2) | <0.001[2] |

[1] P values for within-group comparison from Wilcoxon signed rank test. For between-group comparison of ETC-216, Apo A-I Milano: POPC combined vs. placebo from analysis of covariance of ranks of change from baseline, with the baseline value as a covariate, p = 0.018.
[2] Prespecified primary efficacy end point

TABLE 4

Mean Maximum Atheroma Thickness in the Target Coronary Segment

| Treatment Groups | o. of subjects | Baseline, mm Mean (SD) | Baseline, mm Median (IQR) | Follow-up, mm Mean (SD) | Follow-up, mm Median (IQR) | Change From Baseline, mm Mean (SD) | Change From Baseline, mm Median (95% CI) | P value[1] |
|---|---|---|---|---|---|---|---|---|
| Placebo | 11 | 0.649 (0.317) | 0.683 (0.402-0.846) | 0.641 (0.332) | 0.584 (0.392-0.827) | −0.008 (0.061) | −0.009 (−0.035 to 0.026) | 0.83 |
| ETC-216 15 mg/kg | 21 | 0.815 (0.194) | 0.830 (0.683-0.953) | 0.771 (0.168) | 0.824 (0.646-0.865) | −0.044 (0.094) | −0.049 (−0.079 to −0.015) | 0.03 |
| ETC-216 45 mg/kg | 15 | 0.738 (0.028) | 0.792 (0.531-0.992) | 0.699 (0.269) | 0.758 (0.457-0.963) | −0.039 (0.059) | −0.029 (−0.056 to −0.007) | 0.02 |
| ETC-216 Combined | 36 | 0.783 (0.233) | 0.816 (0.578-0.963) | 0.741 (0.216) | 0.814 (0.552-0.895) | −0.042 (0.080) | −0.035 (−0.058 to −0.020) | <0.001[2] |

[1] P values for within-group comparison from Wilcoxon signed rank test. For between-group comparison of ETC-216, Apo A-I Milano:POPC combined vs. placebo from analysis of covariance of ranks of change from baseline, with the baseline value as a covariate, p = 0.023.
[2] Prespecified primary efficacy end point.

The results showed that ETC-216 is efficacious in reducing plaque size. A statistically significant regression of atherosclerosis was demonstrated in both treatment groups.

6.3. Example 3

Ex vivo Langendorff

This example demonstrates the cardioprotective effect of prophylactic ETC-216 in the reperfused isolated ischemic rabbit heart. Male New Zealand White rabbits, obtained from Charles River weighing approximately 2-3 kg were used in the study. The male New Zealand White rabbit was selected as the appropriate test system for the purposes of this study. The isolated ischemic-reperfused rabbit heart is a model of human myocardial infarction. Upon arrival, animals were assigned unique identification numbers.

Animals were housed in stainless steel cages in accordance with the guidelines of the University of Michigan Committee on the Use and Care of Animals. Veterinary Care provided by the University of Michigan Unit for the Laboratory Animal Medicine. The University of Michigan is accredited by the American Association of Accreditation of Laboratory Animal Health Care, and the animal care use program conforms to the standards in the Guide for the Care and use of Laboratory Animals, DHEW (NIH) Publ. No. 86-23.

ETC-216 is recombinant apolipoprotein A-I Milano/1-palmitoyl-2-oleoyl phosphatidylcholine complex in a one to one ratio by weight. Stock solutions of ETC-216 contained 14 mg protein/ml in a sucrose mannitol buffer. Since the sucrose-mannitol buffer was incompatible with Krebs-Henseleit buffer, and to control for any independent effects of mannitol alone, ETC-216 was dialyzed to obtain a background buffer comprised of 2% glucose in 4 mM sodium phosphate, pH 7.4. The ETC-216 was diluted with Krebs-Henseleit buffer to yield a drug concentration of 0.45 mg/ml. The vehicle was similarly diluted.

Dose selection was based on historical data for doses used in Esperion's Human Phase I single dose safety clinical trials, where doses up to 100 mg/kg of ETC-216 were administered to humans. For the studies outlined in this protocol a concentration of 0.5 mg/ml is approximately equivalent to an intravenous dose of 25 mg/kg administered to a human.

Experiments were conducted using a Langendorff apparatus to perfuse rabbit hearts. Rabbits were rendered unconscious by cervical dislocation and the hearts were removed rapidly and attached to a cannula for perfusion through the aorta. The perfusion medium consisted of a circulating Krebs-Henseleit buffer (pH 7.4, 37° C.; "KH") that was exposed continuously to a mixture of 95% $O_2$/5% $CO_2$ and delivered at a constant rate of 20-25 ml/min. The hearts were paced throughout the protocol via electrodes attached to the right atrium. Pacing stimuli were delivered from a laboratory square wave generator (10% above physiologic pacing, 1 msec duration, Grass 588, Quincy, Mass.). The pulmonary artery was cannulated with Silastic™ tubing to facilitate collection of the pulmonary artery effluent representing the coronary venous return to the coronary sinus. The superior and inferior vena cava and the pulmonary veins were ligated to prevent loss of perfusate from the otherwise severed vessels. A left ventricular drain, thermistor probe, and latex balloon were inserted via the left atrium and positioned in the left ventricle. The fluid filled latex balloon was connected with rigid tubing to a Miller Catheter pressure transducer to permit for measurement of left ventricular developed pressure. The intraventricular balloon is expanded with distilled water to achieve an initial baseline left ventricular end-diastolic pressure of approximately 10 mm Hg. Coronary perfusion pressure was measured with a pressure transducer connected to a side-arm of the aortic cannula. Since the rate of coronary artery perfusion was maintained constant, alterations in the coronary artery perfusion pressure served as an indicator of change in coronary artery resistance. All hemodynamic variables were monitored continuously using a multichannel recorder such as a Grass Polygraph 79D (Quincy, Mass.) interfaced to a Polyview Software Data Acquisition System. Hearts were maintained at 37° C. throughout the experimental period by enclosing the heart in a temperature regulated double lumen glass chamber and passing the perfusion medium through a heated reservoir and delivery system.

Two Treatment groups were used for the Experimental Procedures as shown below.

| Group | Treatment | Test Substance | Conc (mg/ml) |
|---|---|---|---|
| 1 | Ischemia & Reperfusion | Vehicle | 0 |
| 2 | Ischemia & Reperfusion | ETC-216 | 0.45 |

The hearts were experimentally treated as shown in FIG. 5. Isolated hearts were stabilized under normoxic (normal level of oxygen) conditions for 20 minutes before the induction of global ischemia. During the first 10 minutes of this period hearts were exposed to the KH buffer alone, and then for an additional 10 minutes to the KH buffer containing either vehicle (Group 1) or ETC-216 (Group 2). The hearts were then subject to a 30 minute period of ischemia followed by a 60 minute period of reperfusion with KH buffer containing vehicle (Group 1) or ETC-216 (Group 2). Induction of total global ischemia was accomplished by stopping the flow of perfusate to the heart, and reperfusion of the heart was accomplished by turning on the pump to restore the original flow rate.

Aliquots of the pulmonary artery effluent were collected from hearts in all groups at baseline (pre-ischemia), and initially every minute up to 5 minutes, and every 5 minutes thereafter during the reperfusion period. The effluents were analyzed for creatine kinase concentration (FIG. 6), an index of tissue injury. Creatine kinase is a cytosolic enzyme released from irreversibly injured cells. Cardiac functions were continuously monitored (FIG. 7).

Heart end-point determinations were made for:
1-Electrocardiogram—heart rate (paced) to detect for the presence or absence of arrhythmias;
2-Left ventricular developed pressure (FIG. 8) (data shown as mean±standard error of the mean for the indicated number of hearts in each group);
3-Left ventricular dP/dt
4-Left ventricular end-diastolic pressure (FIG. 9) (data shown as mean±standard error of the mean for the indicated number of hearts in each group);
5-Coronary perfusion pressure (FIG. 10) (data shown as mean±standard error of the mean for the indicated number of hearts in each group);
6-Collection of lymphatic drainage to determine release of tissue creatine kinase before and after reperfusion (FIG. 6)

At the conclusion of the experimental protocol, heart biopsies from up to five hearts from each treatment group were immersed immediately in liquid nitrogen and stored at −80° C. for subsequent lipid hydroperoxides analysis. The homogenate samples were normalized to protein content before conducting an assay for lipid peroxides (FIG. 11). ETC-216 reduced cardiac lipid hydroperoxides by 46% in this example.

Upon completion of the designated protocol, two hearts from each group were perfused for 3 minutes with 2.5% glutaraldehyde and 1% $LaCl_3$ in 0.1 M sodium calcodylate buffer (pH 7.4). The osmophilic $LaCl_3$ under normal conditions is retained in the vascular compartment bound to the vessel wall and serves as an indicator of blood vessel integrity. Extravasation of $LaCl_3$ into the extravascular space was used to indicate the presence of vascular injury. Tissue samples from the left ventricular myocardium were removed and cut into segments measuring approximately 1 mm on a side. The samples were fixed for an additional 2 hours at 4° C. in the above mentioned buffer. Thereafter, the samples were dehydrated in an ethanol series and embedded in EM bed-812 (Electron Microscopy Sciences, Ft, Washington, Pa.). Tissue blocs were sectioned with a Reichert ultramicrotome and placed onto formvar-coated copper grids followed by staining with 4% uranyl acetate. Sections were observed with a Phillips CM-10 electron microscope.

Transmission electron microscopy was used to examine myocardial specimens from each of the study groups. The images show that the vehicle-treated hearts' sarcomere structural features are obliterated and contracture bands are present. The mitochondria are markedly swollen with disrupted crystal and osmophilic inclusion bodies. In the ETC-216 treated hearts, the sarcomere structure is relatively normal and the mitochondria appear intact with only minimal swelling. The virtual absence of contraction bands stands in marked contrast with those observed in the control hearts. The ability of ETC-216 to prevent contraction band necrosis is consistent with the observation that hearts pretreated with ETC-216 did not exhibit an increase in LVEDP upon reperfusion. Both contraction band necrosis and a sustained increase in LVEDP are associated with an increase in intracellular calcium overload and irreversible cell injury. The presence of myofibril blurring of the Z-bands, and disruption of the myofibrillar architecture are indicative of extensive damage. Other expected morphological damage included disrupted cristae and matrices of the mitochondria as well as large, electron dense bodies in the mitochondria. The magnification factor was 7900× in both micrographs (FIG. 12).

Analysis of the creatine kinase concentrations (FIG. 6) indicated that the rapid phase of enzyme release into the venous effluent occurs at the time of reperfusion. Control hearts (treated with vehicle) showed a marked release of creatine kinase compared to the ETC-216 treated hearts. In addition, ETC-216 treated hearts showed reduced left ventricular end-diastolic pressure (FIGS. 7 and 9), elevated left ventricular developed pressure (FIG. 8), decreased coronary artery perfusion pressure (FIG. 10) and decreased lipid hydroperoxide (LHP) compared to control hearts (FIG. 11). In addition, ETC-216 protected against morphological changes in the myocardium (FIG. 12). These results demonstrate the cardioprotective effects of ETC-216 when administered prior to the ischemic event.

6.4. Example 4

Acute and Chronic Administration in the LAD Occluded-reperfused Rabbit Heart at 100 mg/kg This example demonstrates the cardioprotective effects of ETC-216 in an in vivo model of regional myocardial ischemia and reperfusion. The male New Zealand White rabbit was selected as the appropriate test system for the purposes of this study because of its lack of collateral blood supply to the heart thus making it unnecessary to employ myocardial blood flow determinations. In this study, different dosing regimens were used in separate groups of rabbits that were subjected to 30 minutes of regional myocardial ischemia by coronary artery ligation and reperfusion. Two dosing regimens were used. In the first protocol, ETC-216 was tested as a single pretreatment in which the heart is exposed to 100 mg/kg of the agent just prior to the onset of regional ischemia, while in the second protocol, two 100 mg/kg pretreatments were administered (one day prior and immediately prior) to the onset of regional ischemia. These protocols are shown in (FIG. 13). This study focused on the effects of ETC-216 as a cardioprotective agent in an in vivo study in which the rabbit heart was subjected to regional myocardial ischemia for a period of 30 minutes followed by reperfusion for a minimum of four hours. This example demonstrates that ETC-216 is a cardioprotective agent when given after the ischemic event.

The procedures used in this study are in agreement with the guidelines of the University of Michigan Committee on the Use and Care of Animals. Veterinary care was provided by the University of Michigan Unit for Laboratory Animal Medicine. The University of Michigan is accredited by the American Association of Accreditation of Laboratory Animal Health Care, and the animal care use program conforms to the standards in the Guide for the Care and use of Laboratory Animals DHEW (NIH) Publ. No. 86-23.

Male New Zealand White rabbits obtained from Charles River weighing approximately 2-3 kg were used in the study. Upon arrival, animals were assigned unique identification numbers. Rabbits were anesthetized with a mixture of xylazine (3.0 mg/kg) and ketamine (35 mg/kg) intramuscularly followed by an intravenous injection of sodium pentobarbital (30 mg/kg). Anesthesia was maintained with intravenous injections of a pentobarbital solution (30 mg/ml). A cuffed endotracheal tube was inserted, and animals were placed on positive-pressure ventilation with room air. The right jugular vein was isolated and cannulated for administration of ETC-216 or a matched volume of vehicle. The right carotid artery was isolated, and instrumented with a MillarTM catheter micro-tip pressure transducer positioned immediately above the aortic valves to monitor aortic blood pressure and to obtain the derived first derivative of the pressure pulse (dP/dt). A lead II electrocardiogram was monitored throughout the experiment. A left thoracotomy and pericardiotomy were performed, followed by identification of the left anterior descending (LAD) coronary artery. A silk suture (3.0; Deknatel, Fall River, Mass.) was passed behind the artery and both ends of the suture were inserted into a short length of polyethylene tubing. Downward pressure on the polyethylene tube while exerting upward tension on the free ends of the suture compresses the underlying coronary artery resulting in occlusion of the vessel and regional myocardial ischemia. The occlusion was maintained for 30 minutes after which the tension on the suture was released and the polyethylene tubing was withdrawn allowing reperfusion to occur. Regional myocardial ischemia was verified by the presence of a region in the area of distribution of the occluded vessel and by changes in the electrocardiogram consistent with the presence of transmural regional myocardial ischemia (ST-segment elevation).

The major end-point determination consisted of measurements of infarct size as a percent of left ventricle and as a percent of the area at risk (FIGS. 14 and 15). At the conclusion of the study, the rabbits, while anesthetized, were given heparin (1,000 U intravenously) after which they were euthanized. The heart was excised, and then prepared to be perfused via the aorta on a Langendorff apparatus with Krebs-Henseleit Buffer at a constant flow of 22-24 ml/min. The hearts were washed with buffer for 10 minutes to ensure that the tissue was clean. Forty-five milliliters of a 1% solution of triphenyltetrazolium chloride (TTC) in phosphate buffer (pH 7.4) was perfused through the heart. TTC demarcates the non-infarcted myocardium within the area at risk with a brick-red color, indicating the presence of formazan precipitate resulting from reduction of TTC by coenzymes present in viable myocardial tissue. Irreversibly injured tissue, lacking the cytosolic dehydrogenases, is unable to form the formazan precipitate and appears pale yellow. The left anterior descending (LAD) artery was ligated in a location identical to the area ligated during the induction of regional myocardial ischemia. The perfusion pump was stopped and 2 ml of a 0.25% solution of Evans Blue was injected slowly through a side-arm port connected to the aortic cannula. The dye was passed through the heart for 10 seconds to ensure equal distribution of the dye. Presence of Evans Blue was used to demarcate the left ventricular tissue that was not subjected to regional ischemia, as opposed to the risk region. The heart was removed from the perfusion apparatus and cut into transverse sections at right angles to the vertical axis. The right ventricle, apex, and atrial tissue were discarded. Both surfaces of each transverse section were traced onto clear acetate sheets. The images were photocopied and enlarged. The photocopies were scanned and downloaded into Adobe PhotoShop (Adobe Systems Inc., Seattle, Wash.). The areas of the normal left ventricle (NLV) non-risk regions, area at risk, and infarct are determined by calculating the number of pixels occupying each area using the Adobe Photo Shop Software. Total area at risk is expressed as the percentage of the left ventricle. Infarct size is expressed as the percentage of the area at risk (ARR) (FIGS. 14 and 15).

The infarct percent of area at risk, infarct percent of left ventricle, and area at risk percent of left ventricle in rabbits treated once (i.e., acute treatment) or treated twice (i.e., chronic treatment) with ETC-216 (100 mg/kg) or an equivalent volume of vehicle. Data are mean±standard error of the mean for n=6 animals per group. Asterisks in FIG. 14 indicate significant difference from the respective control.

Other end-point determinations were made. The ultimate infarct size may be influenced by increases or decreases in myocardial oxygen utilization. Two important determinants of myocardial oxygen compensation are heart rate and pressure load. The rate pressure product (heart rate×mean arterial blood pressure) provides an approximation of a change in myocardial oxygen requirements by the heart. Therefore, the rate-pressure product was calculated to determine if an observed reduction in infarct size correlated with the change in the rate pressure product. The heart rate and mean aortic pressure was monitored continuously throughout the experimental protocol and the data was used to calculate the rate pressure product at specific time points in the study for each of the experimental groups.

The area at risk percent of left ventricle was decreased in ETC-216 treated hearts as compared to controls for both acute and chronic administration, however the results were not statistically significant. The infarct percent of area at risk and the infarct percent of left ventricle were significantly decreased in ETC-216 treated hearts as compared to controls for both acute and chronic administration. These results indicate that ETC-216 is cardioprotective when administered both acutely and chronically.

The creatine kinase activity of myocardial tissue in the risk and non-risk regions can be compared. The principle of the assay is based upon an increase in the absorbance of the reaction mixture at 340 nm as a result of the equimolar reduction of NAD to NADH. The rate of change in absorbance is directly proportional to the creatine kinase activity. One unit is defined as the amount of enzyme that produces one micromole of NADPH per minute under the conditions of the assay procedure.

Myocardial tissue subjected to a prolonged period of blood flow deprivation (ischemia) without reperfusion will undergo morphological changes characteristic of necrosis along with the presence of inflammatory cells. The morphologic appearance of ischemia-induced cell death differs from that occurring as a result of reperfusion. The latter is characterized by contraction bands and is referred to as contraction band necrosis. Heart tissue from each of the groups was preserved and prepared for examination by electron microscopy.

Ischemic reperfusion injury is associated with the accumulation of inflammatory cells, predominantly neutrophils, in the area at risk. Myeloperoxidase (MPO) is an enzyme present almost exclusively in neutrophils (Liu et al., J. Pharmacol. Exp. Ther. 287:527-537, 1998). Therefore, it is anticipated that tissue from the respective regions of the heart can be assayed for MPO activity as an indicator of injury. It is also anticipated that an intervention capable of reducing the inflammatory response would be associated with a reduction in MPO activity in the reperfused risk region when compared to heart tissue from the risk region of non-treated animals. Thus, the percent change in MPO activity (risk region/non-risk region) would be reduced in the drug-treated hearts compared to the control vehicle treated hearts.

At the end of the experiment, tissue myeloperoxidase (MPO) activity was determined in a preliminary, uncontrolled, non-validated assay. Heart tissue samples were obtained from the risk region and the non-risk region and were homogenized in 0.5% hexadecyltrimethyl ammonium bromide and dissolved in 50 mM potassium phosphate buffer, pH 6.0 (see also Liu et al., 1998, *J. Pharmacol. Exp. Ther.* 287: 527-537). Homogenates were centrifuged at 12,500 g at 4° C. for 30 minutes. The supernatants were collected and reacted with 0.167 mg/ml o-dianisidine dihydrochloride (Sigma) and 0.0005 percent H2O2 in 50 mM potassium phosphate buffer, pH 6.0. The change in absorbance was measured spectrophotometrically at 460 nm. One unit of MPO was defined as that quantity of enzyme hydrolyzing 1 mmol of H2O2/minute at 25° C. The results from this preliminary experiment, not presented herein, appear to indicate that there were no differences between ETC-216 and vehicle treated hearts in terms of ischemic reperfusion injury, however, the results have yet to be validated, for example, by comparison of MPO levels prior to ischemic reperfusion injury.

As demonstrated by decreased infarct percent of area at risk and infarct percent of left ventricle, ETC-216 treated hearts were protected from ischemic reperfusion injury. Cardioprotection was conferred by both dosing protocols, that is, ETC-216 administered as a single 100 mg/kg dose prior to the onset of ischemia or ETC-216 administered in two 100 mg/kg doses, one dose given one day prior to ischemia and a second dose given immediately prior to ischemia.

6.5. Example 5

Determination of the Minimal Effective Dose for Acute Administration in the LAD Occluded-reperfused Rabbit Heart This example demonstrates the prophylactic efficacy of various doses of ETC-216 when administered as a single pretreatment just prior to the onset of regional ischemia. The study in example 2 focused on the effects of ETC-216 as a cardioprotective agent in an in vivo study in which the rabbit heart was subjected to regional myocardial ischemia for a period of 30 minutes followed by reperfusion for a minimum of four hours. Two dosing regimens were used. In the first protocol, ETC-216 was tested as a single pretreatment in which the systemic circulation was exposed to 100 mg/kg of the agent just prior to the onset of regional ischemia, while in the second protocol, two 100 mg/kg pretreatments were administered prior to one day prior and immediately prior) to the onset of regional ischemia. Both regimens showed that either one or two treatments with 100 mg/kg ETC-216 is cardioprotective.

Therefore, ETC-216 was tested as a single pretreatment in which the heart was exposed to single doses of the agent or an equivalent volume of vehicle just prior to the onset of regional ischemia to determine effects on cardioprotection. The hearts were analyzed by the same methods used in example 2. In addition, this protocol was designed to find a minimal effect dose of ETC-216 to treat the rabbit heart for protection from ischemia.

To find the minimal effective dose of ETC-216, the same protocol for the acute treatment (See, FIG. 13) was used in which the animals received single treatments of either 10, 3 or 1 mg/kg of ETC-216 or an equivalent volume of vehicle as shown in FIG. 16. The area at risk (AAR) or ischemic region expressed as a percent of the total left ventricle for the 10 mg/kg treatment group was similar in the control group and in the treatment group (FIG. 17). Rabbits treated with 10 mg/kg ETC-216 developed smaller infarcts (p<0.0005) expressed as a percent of the AAR compared to rabbits treated with vehicle (FIG. 18). A reduction in myocardial infarct size (p<0.0001) was also observed when the data were expressed as a percent of the total left ventricle (FIG. 17).

Similar results were observed with a dose of 3 mg/kg. The AAR expressed as a percent of the total left ventricle was similar in the ETC-216-treated and vehicle-treated groups (FIG. 17). Rabbits treated with 3 mg/kg ETC-216 developed smaller infarcts (p<0.05) expressed as a percent of the area at risk compared to rabbits treated with vehicle (FIG. 17). A reduction in myocardial infarct size (p<0.05) was observed when the data were expressed as a percent of the total left ventricle (FIG. 17).

No significant differences were noted with a dose of 1 mg/kg between ETC-216 and vehicle in the size of the AAR when expressed as the percent of the left ventricle (FIG. 17). At 1 mg/kg, no significant differences were noted between groups as a percent of AAR (FIG. 17) and in myocardial infarct size expressed as a percent of the total left ventricle (FIG. 17).

A summary of the data from each of the four acute treatment groups (i.e., 100, 10, 3 and 1 mg/kg) and their respective controls are shown in FIG. 17. The AAR of infarction was similar in each of the four groups. Among the four dosing regimens, infarct size, whether expressed as percent of risk region or percent of the left ventricle, compared to the respective controls was reduced with ETC-216 doses of 100, 10 and 3 mg/kg. In contrast, infarct size in the group of animals receiving 1 mg/kg did not differ from that observed in the respective vehicle-treated group.

FIG. 18 shows examples of temporal changes in lipoprotein unesterified cholesterol. Blood samples were obtained from rabbits just prior to and periodically following administration of 1, 3, 10 or 100 mg/kg ETC-216 or vehicle. Shown are unesterified cholesterol profiles obtained in representative temporal blood serums samples where the serum lipoproteins were separated on the basis of size by gel-filtration chromatography with on-line unesterified cholesterol analysis. Note the rise in high density cholesterol unesterified cholesterol at 45 minutes after administration of ETC-216, especially at 100 mg/kg and to a lesser extent at 10 mg/kg despite the virtual absence of unesterified cholesterol in the intravenously administered ETC-216 test agent. Note also the delayed prominent rise in very low density lipoprotein unesterified cholesterol at 210 and 270 minutes following administration of either 10 mg/kg or 100 mg/kg ETC-216. Note also that changes in lipoprotein unesterified cholesterol were not apparent at the 3 mg/kg ETC-216 treatment dose at the time points assessed, however, this dose was cardioprotective as shown in FIG. 17.

The results demonstrate that 100 mg/kg, 10 mg/kg and 3 mg/kg doses are effective prophylactic doses of ETC-216.

6.6. Example 6

ETC-216 Prevents Ischemia-reperfusion Injury When Administered After the Onset of LAD Occlusion in the Occluded-reperfused Rabbit Heart This example demonstrates the efficacy of ETC-216 in preventing or reducing ischemic reperfusion injury when administered after the ischemic or occlusive event. The studies in Examples 2 and 3 illustrate the prophylactic benefit of treating the heart muscle prior to the onset of ischemia. Therefore to determine if ETC-216 could protect the heart muscle after the onset of ischemia, the LAD was occluded prior to the administration of the test agent or vehicle. In this protocol, ETC-216 was tested as a single treatment in which the heart was exposed to 10 mg/kg of the agent or an equivalent volume of vehicle administered during the last 5 minutes of regional ischemia and continued through the first 55 minutes of reperfusion (FIG. 19). The AAR or ischemic region expressed as a percent of the total left ventricle for the 10 mg/kg treatment group was similar in the control group (FIG. 20). Rabbits treated with ETC-216 developed smaller infarcts (p<0.001) expressed as a percent of the AAR compared to rabbits treated with vehicle (FIG. 20). A reduction in myocardial infarct size (p<0.0005) also was observed when the data were expressed a percent of the total left ventricle (FIG. 20).

This example demonstrates that a single treatment administered after an ischemic event, mitigated or decreased ischemic reperfusion injury.

Various embodiments of the invention have been described. The descriptions and examples are intended to be illustrative of the invention and not limiting indeed, it will be apparent to those of skill in the art that modifications may be made to the various embodiments of the invention described without departing from the spirit of the invention or scope of the appended claims set forth below.

All references cited herein are hereby incorporated by reference in their entireties.

We claim:

1. A method of treating coronary atherosclerosis in a subject in need thereof, said method comprising administering an Apolipoprotein A-I Milano: 1-palmitoyl-2-oleoyl-sn-glycero-3-phosphocholine complex (Apo A-IM:POPC complex) at a dose of about 1 mg of protein/kg to about 100 mg of protein/kg, and wherein said method regresses coronary atherosclerosis.

2. The method of claim 1 wherein the Apo A-1M:POPC complex is administered to a subject at a dose of about 15 mg/kg or 45 mg/kg.

3. The method of claim 1 wherein the Apo A-IM:POPC complex is administered to a subject at a dose of about 15 mg/kg to about 45 mg/kg.

4. The method of claim 1 wherein the Apo A-I Milano is recombinant Apo A-I Milano.

5. The method of claim 1 wherein the Apo A-IM:POPC complex is comprised of Apolipoprotein A-I Milano and 1-palmitoyl-2-oleoyl-sn-glycero-3-phosphocholine in a ratio of about 1:1 wt protein/wt lipid.

6. The method of claim 1 wherein the Apo A-IM:POPC complex is a sterile liquid pharmaceutical formulation.

7. The method of claim 6 wherein the pharmaceutical formulation is administered to a subject at a dose of about 15 mg/kg or 45 mg/kg.

8. The method of claim 6 wherein the pharmaceutical formulation is administered to a subject once weekly for about 6 months, about 5 months, about 4 months, about 3 months, about 2 months or about 1 month.

9. The method of claim 6 wherein the pharmaceutical formulation is administered to a subject about every day for about 1 month.

10. The method of claim 6 wherein the pharmaceutical formulation is administered to a subject about every 3 days for about 1 month to about 6 months.

11. The method of claim 6 wherein the pharmaceutical formulation is administered about every 10 days for about 1 month to about 6 months.

12. The method of claim 6 wherein the pharmaceutical formulation is administered about every 14 days for about 1 month to about 6 months.

13. The method of claim 1 further comprising surgical intervention.

14. The method of claim 13 wherein the surgical intervention comprises percutaneous transluminal coronary angioplasty or coronary artery bypass grafting.

15. The method of claim 1 further comprising administration of another drug to treat or ameliorate the diseases, disorders, symptoms or pain associated with acute coronary syndromes.

16. The method of claim 1 wherein the percent atheroma volume in a subject's affected vessel is reduced by about −0.73% to about −1.29%.

17. The method of claim 1 wherein the total atheroma volume in the target vessel of the subject is reduced by about −15.1 mm$^3$ to about −12.6 mm$^3$.

18. The method of claim 1 wherein the mean maximum atheroma thickness in the subject's target coronary segment is reduced by about −0.039 mm to −0.044 mm.

19. The method of claim 6 wherein the pharmaceutical formulation is administered intravenously.

20. The method of claim 19 wherein the pharmaceutical formulation is administered over about one hour.

21. The method of claim 19 wherein the pharmaceutical formulation is administered over about three hours.

22. The method of claim 6 wherein the pharmaceutical formulation comprises Apo A-I Milano, POPC, a sucrose-mannitol carrier and a phosphate buffer.

23. The method of claim 22 wherein the sucrose-mannitol carrier consists of about 6.0% to about 6.4% sucrose and about 0.8% to about 1% mannitol.

24. The method of claim 23 wherein the sucrose-mannitol carrier consists of about 6.2% sucrose and about 0.9% mannitol.

25. The method of claim 6 wherein the pharmaceutical formulation has a pH of about 7.0 to about 7.8.

26. The method of claim 25 wherein the pH is about 7.5.

27. The method of claim 6 wherein the pharmaceutical formulation comprises about 12 mg/ml to about 18 mg/ml Apo A-I Milano.

28. The method of claim 6 wherein the pharmaceutical formulation comprises about 11 mg/ml to about 17 mg/ml of POPC.

29. The method of claim 6 wherein the pharmaceutical formulation comprises less than 6,000 particulates greater than 10 μm in size per 50 mL.

30. The method of claim 6 wherein the pharmaceutical formulation comprises less than 600 particulates greater than 25 μm in size per 50 mL.

31. The method of claim 6 wherein the pharmaceutical formulation has an Osmolality of about 280 to about 320 mOsm.

32. The method of claim 31 wherein the pharmaceutical formulation has an Osmolality of about 290 mOsm.

33. The method of claim 1, wherein said method provides for the promotion of cholesterol efflux from affected vessels.

34. The method of claim 1, wherein said method provides for reverse cholesterol transport.

35. The method of claim 1, wherein said method provides for decreased atheroma volume in an affected vessel.

36. The method of claim 1, wherein said method provides for a decrease in total plaque volume of an affected vessel.

37. The method of claim 1, wherein said method provides for a decrease in the average maximal plaque thickness in an affected vessel.

38. The method of claim 1, wherein said method provides for a decrease in average maximal atheroma thickness.

39. The method of claim 1, wherein said method provides for a decrease in plaque volume in least percent area.

40. The method of claim 1, wherein said method provides for a decrease in the greatest percent plaque area.

41. The method of claim 1, wherein said method provides for an increase mean coronary luminal diameter in an affected vessel.

42. The method of claim 1, wherein said method provides for decreased angiographic lesions as compared to a subject not receiving said treatment.

43. The method of claim 1, wherein said method provides for achieving patency of an occluded vessel or of maintaining patency of an occluded vessel.

44. A method of treating acute coronary syndromes in a subject in need thereof, said method comprising administering an Apolipoprotein A-I Milano: 1-palmitoyl-2-oleoyl-sn-glycero-3-phosphocholine complex (Apo A-IM:POPC complex) at a dose of about 1 mg of protein/kg to about 100 mg of protein/kg, and wherein said method ameliorates disorders associated acute coronary syndromes.

45. The method of claim 44, wherein said method provides for the promotion of cholesterol efflux from affected vessels.

46. The method of claim 44, wherein said method provides for reverse cholesterol transport.

47. The method of claim 44, wherein said method provides for decreased atheroma volume in an affected vessel.

48. The method of claim 44, wherein said method provides for a decrease in total plaque volume of an affected vessel.

49. The method of claim 44, wherein said method provides for a decrease in the average maximal plaque thickness in an affected vessel.

50. The method of claim 44, wherein said method provides for a decrease in average maximal atheroma thickness.

51. The method of claim 44, wherein said method provides for a decrease in plaque volume in least percent area.

52. The method of claim 44, wherein said method provides for a decrease in the greatest percent plaque area.

53. The method of claim 44, wherein said method provides for an increase mean coronary luminal diameter in an affected vessel.

54. The method of claim 44, wherein said method provides for decreased angiographic lesions as compared to a subject not receiving said treatment.

55. The method of claim 44, wherein said method provides for achieving patency of an occluded vessel or of maintaining patency of an occluded vessel.

* * * * *